(12) United States Patent
Gupta et al.

(10) Patent No.: US 9,150,877 B2
(45) Date of Patent: Oct. 6, 2015

(54) **CONSTRUCT AND METHOD FOR EXPRESSING TRANSGENES USING A *BRASSICA* BIDIRECTIONAL CONSTITUTIVE PROMOTER**

(71) Applicant: Dow AgroSciences LLC, Indianapolis, IN (US)

(72) Inventors: Manju Gupta, Carmel, IN (US); Sean Michael Russell, Carmel, IN (US); Liu Yin Shen, Westfield, IN (US); Sivarama Reddy Chennareddy, West Lafayette, IN (US); Jyoti Rout, Portland, OR (US); Stephen Novak, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 367 days.

(21) Appl. No.: 13/653,602

(22) Filed: Oct. 17, 2012

(65) Prior Publication Data

US 2013/0104257 A1    Apr. 25, 2013

Related U.S. Application Data

(63) Continuation-in-part of application No. 12/284,888, filed on Sep. 25, 2008, now Pat. No. 8,399,218.

(60) Provisional application No. 61/656,634, filed on Jun. 7, 2012, provisional application No. 60/995,557, filed on Sep. 27, 2007.

(51) Int. Cl.
| | |
|---|---|
| *C12N 15/113* | (2010.01) |
| *C12N 15/82* | (2006.01) |
| *C12N 9/10* | (2006.01) |

(52) U.S. Cl.
CPC .......... *C12N 15/8278* (2013.01); *C12N 9/1092* (2013.01); *C12N 15/113* (2013.01); *C12N 15/8243* (2013.01); *C12N 15/8274* (2013.01); *C12N 15/8275* (2013.01); *C12Y 205/01019* (2013.01); *C07K 2319/00* (2013.01); *C07K 2319/81* (2013.01); *C12N 2830/205* (2013.01)

(58) Field of Classification Search
None
See application file for complete search history.

(56) References Cited

U.S. PATENT DOCUMENTS

| | | | |
|---|---|---|---|
| 6,388,170 B1 | 5/2002 | Gan et al. | |
| 6,867,293 B2 * | 3/2005 | Andrews et al. | 536/23.6 |
| 7,026,526 B2 * | 4/2006 | Snell | 800/278 |
| 7,053,265 B2 | 5/2006 | Kapranov et al. | |
| 7,129,343 B2 | 10/2006 | Li et al. | |
| 2006/0162020 A1 * | 7/2006 | Sauer et al. | 800/282 |

OTHER PUBLICATIONS

GenBank Accession No. AC241089.1. BRassica rapa subsp. pekinensis clone KBrH003H2O. Published May 31, 2010. pp. 1-24.*

Kim et al. A 20 nucleotide upstream element is essential for the nopaline synthase (nos) promoter activity. Plant Molecular Biology. 1994. 24: 105-117.*

Benfey et al. Sequence requirements of the 5-enolpyryvylshikimate-3-phosphate synthase 5'-upstream region for tissue-specific expression in flowers and seedlings. The Plant Cell. 1990. 2: 849-856.*

Marsolier et al. Multiple functions of promoter sequences involved in organ-specific expression and ammonia regulation of a cytosolic soybean glutamine synthetase gene in transgenic Lotus corniculatus. The Plant Journal. 1993. 3(3): 405-414.*

International Search Report, International Application No. PCT/US2013/044262, mailed Jan. 15, 2014, 6 pages.

National Academy of Agricultural Science, Brassica rapa Subsp. pekinesis Clone KBrH003H2O. May 31, 2010. GenBank Acession No. AC241089.1, Accessed from http://www.ncbi.nlm.nih.gov/nuccore/AC241089 on Dec. 29, 2013.

* cited by examiner

*Primary Examiner* — Anne Kubelik
*Assistant Examiner* — Ashley K Buran
(74) *Attorney, Agent, or Firm* — Yung H. Lee; Barnes & Thornburg LLP

(57) ABSTRACT

Provided are constructs and methods for expressing multiple genes in plant cells and/or plant tissues using a disclosed bidirectional promoter from *Brassica napus* or *Brassica* bidirectional constitutive promoter (BBCP). The constructs provided comprise at least one such bi-directional promoter linked to multiple gene expression cassettes, wherein each of the gene expression cassettes comprises at least one transgene. In some embodiments, the constructs and methods provided allow expression of genes between two and twenty.

26 Claims, No Drawings

SEQUENCE LISTING

<160> NUMBER OF SEQ ID NOS: 33

<210> SEQ ID NO 1
<211> LENGTH: 739
<212> TYPE: DNA
<213> ORGANISM: Brassica napus

<400> SEQUENCE: 1

```
acagagagaa aggaatatgc tttcgtagga agtgaacgaa aaagaaatgg ttaagctcaa      60
tacttgctcg gattctaaac caaattgaga gagagttccg aattgccgtg gtttatccta     120
aaccgaacct cagatcggtt tgattgtttg gggtttgtga catatataac tggaaaaaga     180
catcccccgg tttgattatg ttccaaactc taaaccagat tgagattatt ttccgataag     240
cttatacatt cctgtcgggt attttcggat atgtttgaat cttggataat atccgatccg     300
aaccggtacc cgaaacataa atgaaagcat acccaatcgg atatttcacc atatctagat     360
ccgacctaga acccgatttt ttggatcgga tccagacatg gatgttacca tcgtcttcga     420
ttaaaggtaa tctggccggt tactcttcga tttatgtttc ctctccaata ttctagtagt     480
aaaccgcaat cgattatttta tgagttagat tggttcatgg gttttttgtgt aaaaaggcc     540 cagtaacttc ttggaggccc attttaaaac caccaaatct taacccttc aagtcttcac      600 ctaaccaaaa ccttccttcc cacttgctgt ctgtaacacg tggcaggttc tcattggcta     660
ataggaaatg ctcatacacc atcgtttgag gtgggttggt gaaggatttt gatggctacc     720
ttcttcgtca ccaaacccc                                                  739

<210> SEQ ID NO 2
<211> LENGTH: 1232
<212> TYPE: DNA
<213> ORGANISM: Artificial Sequence
<220> FEATURE:
<223> OTHER INFORMATION: Full promoter including the addition of a NcoI
      restriction enzyme site

<400> SEQUENCE: 2
catggacttg aaaactgaat ctctctgttt cagacaaaac cctcctacaa agaatgttcc      60
ttttcagaca aaacccaac taatattcta gatcttgaag tgaatcatca tcatcatcaa      120
acccgtaaag atctttctag tgtctacagt gttagttccc ctataaagtt cacagctttt     180
tcgaatgagg ctcgagtata gtggtgatct gaatctagag tttcagatgg aagacaaaag     240
agatcacctg gaatgattta gctttgtgtc tgtgtataca gcactattca gacaggaaga     300
agcttcgcgt cgaataatgt ttttgatcag ctttcacgcc acgtaagtag aagaaaacga     360
aacatcaagc agctctaagc cggatccttt tttagcccgg aggtgaagga gatacagaga     420
gaaaggaata tgctttcgta ggaagtgaac gaaaaagaaa tggttaagct caatacttgc     480
tcggattcta aaccaaattg agagagagtt ccgaattgcc gtggtttatc ctaaaccgaa     540
cctcagatcg gtttgattgt ttggggtttg tgacatatat aactggaaaa agacatcccc     600
cggtttgatt atgttccaaa ctctaaacca gattgagatt attttccgat aagcttatac     660
attcctgtcg ggtattttcg gatatgtttg aatcttggat aatatccgat ccgaaccggt     720
acccgaaaca taaatgaaag catacccaat cggatatttc accatatcta gatccgacct     780
agaacccgat tttttggatc ggatccagac atggatgtta ccatcgtctt cgattaaagg     840
taatctggcc ggttactctt cgatttatgt ttcctctcca atattctagt agtaaaccgc     900
aatcgattat ttatgagtta gattggttca tgggttttg tgttaaaaag gcccagtaac     960
ttcttggagg cccattttaa aaccaccaaa tcttaaccct tcaagtctt cacctaacca    1020 aaaccttcct tcccacttgc tgtctgtaac acgtggcagg ttctcattgg ctaataggaa    1080
atgctcatac accatcgttt gaggtgggtt ggtgaaggat tttgatggct accttcttcg    1140
tcaccaaacc ccctctaaag tttattaaat ctgaggaaga cagagagtgg gtttaggtga    1200
gcgagtccaa agatcgaaac ttttctcca tg                                   1232
```

```
<210> SEQ ID NO 3
<211> LENGTH: 1232
<212> TYPE: DNA
<213> ORGANISM: Artificial Sequence
<220> FEATURE:
<223> OTHER INFORMATION: Reverse complement of full promoter with the
      addition of nucleotide sequences to include a restriction site

<400> SEQUENCE: 3
catggagaaa aagtttcgat ctttggactc gctcacctaa acccactctc tgtcttcctc      60
agatttaata aactttagag ggggtttggt gacgaagaag gtagccatca aaatccttca     120
ccaacccacc tcaaacgatg gtgtatgagc atttcctatt agccaatgag aacctgccac     180
gtgttacaga cagcaagtgg gaaggaaggt tttggttagg tgaagacttg aaagggttaa     240
gatttggtgg ttttaaaatg ggcctccaag aagttactgg gccttttttaa cacaaaaacc     300 catgaaccaa tctaactcat aaataatcga ttgcggttta ctactagaat attggagagg     360
aaacataaat cgaagagtaa ccggccagat taccttttaat cgaagacgat ggtaacatcc     420
atgtctggat ccgatccaaa aaatcgggtt ctaggtcgga tctagatatg gtgaaatatc     480
cgattgggta tgctttcatt tatgtttcgg gtaccggttc ggatcggata ttatccaaga     540
ttcaaacata tccgaaaata cccgacagga atgtataagc ttatcggaaa ataatctcaa     600
tctggtttag agtttggaac ataatcaaac cggggatgt cttttttccag ttatatatgt     660 cacaaacccc aaacaatcaa accgatctga ggttcggttt aggataaacc acggcaattc     720
ggaactctct ctcaatttgg tttagaatcc gagcaagtat tgagcttaac catttctttt     780
tcgttcactt cctacgaaag catattcctt tctctctgta tctccttcac ctccgggcta     840
aaaaaggatc cggcttagag ctgcttgatg tttcgttttc ttctacttac gtggcgtgaa     900
agctgatcaa aaacattatt cgacgcgaag cttcttcctg tctgaatagt gctgtataca     960
cagacacaaa gctaaatcat ccaggtgat ctcttttgtc ttccatctga aactctagat    1020
tcagatcacc actatactcg agcctcattc gaaaaagctg tgaactttat aggggaacta    1080
acactgtaga cactagaaag atctttacgg gtttgatgat gatgatgatt cacttcaaga    1140
tctagaatat tagttgggtt tttgtctgaa aaggaacatt ctttgtagga gggttttgtc    1200
tgaaacagag agattcagtt ttcaagtcca tg                                  1232

<210> SEQ ID NO 4
<211> LENGTH: 4760
<212> TYPE: DNA
<213> ORGANISM: Artificial Sequence
<220> FEATURE:
<223> OTHER INFORMATION: Bidirectional promoter sequence

<400> SEQUENCE: 4
cgacggcccg ggctggttct tcgcagctgg atcaaacgag taagcaagcc tgtgcaataa      60
ccatatagac tttgctagct tcaaaaaggc ctgataaaac gcggtcctcg ggtgcccccc     120
tcctgtcacg tactcacgct ggtctaggtt tccaaagaaa gaagcttcca tctttgggtg     180
gatcaagatg agatacttgc tcctgcagaa cttaccaaag ttggaatcag ggtttgtagc     240
cagagcatct agtggatcca tatccttttaa agcaagaaac tgagtgaaga aggtctcagt     300
gtcattatct gagtctaatg agaaagtctc ctgctgaaac ccactgaaca tcctctggca     360
tatgtatgac tcaaacgcat acttcttgtg aggcctcttg gcgtaagcaa caccaggctc     420
aatggactca gctgcagaat caagatccca tcccgcagct ttcatcatgt tgatcaacgg     480
```

```
ctttgagaaa tcgtgaacag ctttagaagc agcttcatat gtagattcaa aaagcgcaat    540
ggtcaagtca ggaaactgca aatcaccgga agattcgtta gtggacgaca ttcctcttaa    600
cttaagattc ttctcgagct taagacgttt ctgattagct tcctcgatct tctccaacat    660
atgagtgatc tcggagtcct tgttctgaat ctcagactga aacttcttca ccatgacctc    720
gtaagtcttc aacagactct gctgctcttg gatctctgcg gctagacgag agtctttggg    780
agagacgcac acaggcttgg ggttgttctc tctgtaaaca tgtttcagct cggagagatt    840
cttgagttcg gagatcacag ccttgtcggc ttcctgaatc ttgtcggggt cgtaaggagt    900
gtgagcagat tgaagctgga tgtaagcaga ttttagagaa gagatgtttc caaagaggtt    960
ggagataagt gcttccatag cttcagggtt ttggttgata cattgttcca ttggttgagg   1020
atggaccttc tggttgttgt tgttgttgtt gagttgagtt tctttcaacc cacttggtag   1080
catacttgaa aactgaatct ctctgtttca gacaaaaccc tcctacaaag aatgttcctt   1140
ttcagacaaa aacccaacta atattctaga tcttgaagtg aatcatcatc atcatcaaac   1200
ccgtaaagat ctttctagtg tctacagtgt tagttcccct ataaagttca cagcttttc    1260 gaatgaggct cgagtatagt ggtgatctga atctagagtt tcagatggaa gacaaaagag   1320
atcacctgga atgatttagc tttgtgtctg tgtatacagc actattcaga caggaagaag   1380
cttcgcgtcg aataatgttt ttgatcagct ttcacgccac gtaagtagaa gaaaacgaaa   1440
catcaagcag ctctaagccg gatccttttt tagcccggag gtgaaggaga tacagagaga   1500
aaggaatatg ctttcgtagg aagtgaacga aaaagaaatg gttaagctca atacttgctc   1560
ggattctaaa ccaaattgag agagagttcc gaattgccgt ggtttatcct aaaccgaacc   1620
tcagatcggt ttgattgttt ggggtttgtg acatatataa ctggaaaaag catcccccg    1680 gtttgattat gttccaaact ctaaaccaga ttgagattat tttccgataa gcttatacat   1740
tcctgtcggg tattttcgga tatgtttgaa tcttggataa tatccgatcc gaaccggtac   1800
ccgaaacata aatgaaagca tacccaatcg gatatttcac catatctaga tccgacctag   1860
aacccgattt tttggatcgg atccagacat ggatgttacc atcgtcttcg attaaaggta   1920
atctggccgg ttactcttcg atttatgttt cctctccaat attctagtag taaaccgcaa   1980
tcgattattt atgagttaga ttggttcatg gttttttgtg ttaaaaaggc ccagtaactt   2040
cttggaggcc cattttaaaa ccaccaaatc ttaacccttt caagtcttca cctaaccaaa   2100
accttccttc ccacttgctg tctgtaacac gtggcaggtt ctcattggct aataggaaat   2160
gctcatacac catcgtttga ggtgggttgg tgaaggattt tgatggctac cttcttcgtc   2220
accaaacccc ctctaaagtt tattaaatct gaggaagaca gagagtgggt ttaggtgagc   2280
gagtccaaag atcgaaactt tttctccaat ggcgcaagct agcagaatct gccatggcgt   2340
gcagcagaac ccatgtgcta tctccaatct ctccaaatca aaccaccgca aatctccctt   2400
ctctgtctcg ctgaagacgc accagcagca gcgtggagct tatcagatat cttcgcgggg   2460
gttgaagaag agcgcgatgg tgctaaaccg ttctgtaact cgtccggtta aggttatggc   2520
ctctgtttcc acggcggaga aagcttcgga gattgtgctt caacccatta gagaaatctc   2580
gggtctgatc aagctacccg gatccaaatc tctgtccaac cggattcttc ttcttgccgc   2640
tttatccgag gtttgcttct ttctttgttt gcttagtgtt gcgttttaa cggcgtgagg    2700 atgaagaaag gttctgactt tgttgtggtt ttatagggaa ctactgtagt tgacaacttg   2760
ttgaacagtg atgacattaa ctacatgctt gatgcgttga acaagttggg gcttaatgtg   2820
gaacgtgaca gtgagaacaa ccgtgcggtt gttgaaggat gtggcgggat attcccagct   2880
```

```
tctttagatt ctaagggtga tatcgagttg taccttggga atgcaggaac agccatgcgt    2940
ccacttacag ctgcagttac tgctgctggt ggcaacgcaa ggtaaggtta aggacttatt    3000
ctgttagtta gttttgatta ttttaagaat cggtcttgta ctgatgcttt ttagttgggt    3060
ttgtttacca gttatgtgct tgatggggtg cctagaatga gggaaagacc tataggagat    3120
ttggttgttg gtcttaagca gcttggtgct gatgttgaat gtactcttgg tactaactgt    3180
cctcctgttc gtgtcaatgc taatggtggc ctgcccggtg aaaggtgag tttgtaattt     3240
cagcatttgc tatgtgaaaa gttgcagcaa tctttgttca tcacactgcg ttagcttgac    3300
atgattttag cttttgtatg gtttcttgat tgacacatta gacatgtttt tgcattttc    3360
aggtgaagct ttctggatca atcagtagtc aatacttgac tgcactgctc atggcagctc    3420
ccttagctct tggagacgtt gagattgaga tcattgataa attgatttct gttccatatg    3480
ttgaaatgac attgaagttg atggaacgtt ttggtgttag tgccgagcat agtgacagtt    3540
gggatcgttt ctttgtcaag ggcggtcaga aatacaagta agagttgttt ctaaaatcac    3600
tgaacttata attagattga cagaagagtg actaaccaaa tggtaaaatt tgattcaggt    3660
cgcctggtaa tgcttacgta gaaggtgatg cttctagtgc tagttatttc ttggctggtg    3720
ctgccattac tggtgaaacc gttactgttg aaggttgtgg aacaaccagc ctgcaggtaa    3780
cactaagttt ataataaaat ttgcttagtt caattttttt ttgtctttct aaggcttggc    3840
tagttgtgtc acttgtgtgt aacatatgaa gaatctaagt ttagtttttt ttggtgatga    3900
atctcaaagg gagatgtgaa gttcgctgag gttcttgaga aaatgggatg taaagtgtca    3960
tggacagaga acagtgtgac tgtgactgga ccatctagag atgcttttgg aatgagacac    4020
ttgcgtgctg ttgatgtcaa catgaacaaa atgcctgatg tagccatgac tcttgccgtt    4080
gtagctctct ttgcagatgg cccaaccacc attagagatg gtaagcacac cctctaattg    4140
tttttttaa agattcatag tcacttagtt ctccctctcat ccattctttt ttatcatata    4200
tagtggctag ctggagagta aaggagacag aaaggatgat tgccatttgc acagagctta    4260
ggaaggtaaa acatttttct ttctgtctcg ctctcactct cactctcttg gttttatgtg    4320
ctcagtctaa gttaagttct gcataacttt tgcgtacagc ttggagctac agtggaagag    4380
ggttcagatt attgtgtgat aactccacca gcaaagctga aaccggcgga gattgacaca    4440
tatgatgacc atagaatggc aatggcattc tcccttgcag cttgtgctga tgttccagtg    4500
accatcaaag atcctggttg taccaggaaa actttccctg actacttcca gtccttgaa    4560
agtatcacaa agcactaaaa aaacccttt tttttaccac tgcactaaaa agaccttaaa    4620
gcccatttgt cttttctttt tgatccaatt gagatcagtt tcctctgttg tcactgtaag    4680
attacgaaaa acaaagagta ttaagattgc ttgcttgtac cttaaactgt ttgatgcaat    4740
cgttgaatca gttttgggcc                                                4760
```

<210> SEQ ID NO 5
<211> LENGTH: 361
<212> TYPE: PRT
<213> ORGANISM: Brassica napus

<400> SEQUENCE: 5

Met Leu Pro Ser Gly Leu Lys Glu Thr Gln Leu Asn Asn Asn Asn Asn
1               5                   10                  15

Asn Gln Lys Val His Pro Gln Pro Met Glu Gln Cys Ile Asn Gln Asn
            20                  25                  30

| | | | | | | | | | | | | |
|---|---|---|---|---|---|---|---|---|---|---|---|---|
|Pro|Glu|Ala|Met|Glu|Ala|Leu|Ile|Ser|Asn|Leu|Phe|Gly|Asn|Ile|Ser|
| | |   35|   |   |   |   40|   |   |   |   |   45|   |   |   |   |

Pro Glu Ala Met Glu Ala Leu Ile Ser Asn Leu Phe Gly Asn Ile Ser
            35                      40                      45

Ser Leu Lys Ser Ala Tyr Ile Gln Leu Gln Ser Ala His Thr Pro Tyr
 50                      55                      60

Asp Pro Asp Lys Ile Gln Glu Ala Asp Lys Ala Val Ile Ser Glu Leu
 65                      70                      75                      80

Lys Asn Leu Ser Glu Leu Lys His Val Tyr Arg Glu Asn Asn Pro Lys
                     85                      90                      95

Pro Val Cys Val Ser Pro Lys Asp Ser Arg Leu Ala Ala Glu Ile Gln
                100                     105                     110

Glu Gln Gln Ser Leu Leu Lys Thr Tyr Glu Val Met Val Lys Lys Phe
            115                     120                     125

Gln Ser Glu Ile Gln Asn Lys Asp Ser Glu Ile Thr His Met Leu Glu
130                     135                     140

Lys Ile Glu Glu Ala Asn Gln Lys Arg Leu Lys Leu Glu Lys Asn Leu
145                     150                     155                     160

Lys Leu Arg Gly Met Ser Ser Thr Asn Glu Ser Ser Gly Asp Leu Gln
                    165                     170                     175

Phe Pro Asp Leu Thr Ile Ala Leu Phe Glu Ser Thr Tyr Glu Ala Ala
            180                     185                     190

Ser Lys Ala Val His Asp Phe Ser Lys Pro Leu Ile Asn Met Met Lys
            195                     200                     205

Ala Ala Gly Trp Asp Leu Asp Ser Ala Ala Glu Ser Ile Glu Pro Gly
            210                     215                     220

Val Ala Tyr Ala Lys Arg Pro His Lys Lys Tyr Ala Phe Glu Ser Tyr
225                     230                     235                     240

Ile Cys Gln Arg Met Phe Ser Gly Phe Gln Gln Glu Thr Phe Ser Leu
                    245                     250                     255

Asp Ser Asp Asn Asp Thr Glu Thr Phe Phe Thr Gln Phe Leu Ala Leu
                    260                     265                     270

Lys Asp Met Asp Pro Leu Asp Ala Leu Ala Thr Asn Pro Asp Ser Asn
            275                     280                     285

Phe Gly Lys Phe Cys Arg Ser Lys Tyr Leu Ile Leu Ile His Pro Lys
            290                     295                     300

Met Glu Ala Ser Phe Phe Gly Asn Leu Asp Gln Arg Glu Tyr Val Thr
305                     310                     315                     320

Gly Gly Gly His Pro Arg Thr Ala Phe Tyr Gln Ala Phe Leu Lys Leu
                    325                     330                     335

Ala Lys Ser Ile Trp Leu Leu His Arg Leu Ala Tyr Ser Phe Asp Pro
            340                     345                     350

Ala Ala Lys Asn Gln Pro Gly Pro Ser
            355                     360

<210> SEQ ID NO 6
<211> LENGTH: 1083
<212> TYPE: DNA
<213> ORGANISM: Brassica napus
<220> FEATURE:
<221> NAME/KEY: misc_feature
<222> LOCATION: (279)..(280)
<223> OTHER INFORMATION: n is a, c, g, or t

<400> SEQUENCE: 6
atgctaccaa gtgggttgaa agaaactcaa ctcaacaaca acaacaacaa ccagaaggtc     60
catcctcaac caatggaaca atgtatcaac caaaaccctg aagctatgga agcacttatc    120

-continued

```
tccaacctct ttggaaacat ctcttctcta aatctgctt acatccagct tcaatctgct    180
cacactcctt acgaccccga caagattcag gaagccgaca aggctgtgat ctccgaactc   240
aagaatctct ccgagctgaa acatgtttac agagagaann accccaagcc tgtgtgcgtc   300
tctcccaaag actctcgtct agccgcagag atccaagagc agcagagtct gttgaagact   360
tacgaggtca tggtgaagaa gtttcagtct gagattcaga caaggactc cgagatcact    420
catatgttgg agaagatcga ggaagctaat cagaaacgtc ttaagctcga agaatctt     480
aagttaagag gaatgtcgtc cactaacgaa tcttccggtg atttgcagtt tcctgacttg   540
accattgcgc tttttgaatc tacatatgaa gctgcttcta agctgttca cgatttctca    600
aagccgttga tcaacatgat gaaagctgcg ggatgggatc ttgattctgc agctgagtcc   660
attgagcctg gtgttgctta cgccaagagg cctcacaaga gtatgcgtt tgagtcatac    720
atatgccaga ggatgttcag tgggtttcag caggagactt tctcattaga ctcagataat   780
gacactgaga ccttcttcac tcagtttctt gctttaaagg atatggatcc actagatgct   840
ctggctacaa accctgattc aactttggt aagttctgca ggagcaagta tctcatcttg    900
atccacccaa agatggaagc ttctttcttt ggaaacctag accagcgtga gtacgtgaca   960
ggagggggc acccgaggac cgcgttttat caggcctttt tgaagctagc aaagtctata   1020
tggttattgc acaggcttgc ttactcgttt gatccagctg cgaagaacca gcccgggccg  1080
tcg                                                                1083
```

<210> SEQ ID NO 7
<211> LENGTH: 1571
<212> TYPE: DNA
<213> ORGANISM: Brassica napus

<400> SEQUENCE: 7

```
gcagcagcgt ggagcttatc agatatcttc gcggggttg aagaagagcg cgatggtgct    60
aaaccgttct gtaactcgtc cggttaaggt tatgcctct gtttccacgg cggagaaagc   120
ttcggagatt gtgcttcaac ccattagaga atctcgggt ctgatcaagc tacccggatc    180
caaatctctg tccaaccgga ttcttcttct tgccgcttta tccgaggtt gcttcttct    240
ttgtttgctt agtgttgcgt ttttaacggc gtgaggatga agaaaggttc tgactttgtt   300
gtggttttat agggaactac tgtagttgac aacttgttga acagtgatga cattaactac   360
atgcttgatg cgttgaacaa gttggggctt aatgtggaac gtgacagtga gaacaaccgt   420
gcggttgttg aaggatgtgg cgggatattc ccagcttctt tagattctaa gggtgatatc   480
gagttgtacc ttgggaatgc aggaacagcc atgcgtccac ttacagctgc agttactgct   540
gctggtggca acgcaaggta aggttaagga cttattctgt tagttagttt tgattatttt   600
aagaatcggt cttgtactga tgctttttag ttgggtttgt ttaccagtta tgtgcttgat   660
ggggtgccta gaatgaggga aagacctata ggagatttgg ttgttggtct taagcagctt   720
ggtgctgatg ttgaatgtac tcttggtact aactgtcctc ctgttcgtgt caatgctaat   780
ggtggcctgc ccggtggaaa ggtgagtttg taatttcagc atttgctatg tgaaaagttg   840
cagcaatctt tgttcatcac actgcgttag cttgacatga ttttagcttt tgtatggttt   900
cttgattgac acattagaca tgttttgca tttttcaggt gaagctttct ggatcaatca   960
gtagtcaata cttgactgca ctgctcatgg cagctcccctt agctcttgga gacgttgaga  1020
ttgagatcat tgataaattg atttctgttc catatgttga aatgacattg aagttgatgg   1080
aacgttttgg tgttagtgcc gagcatagtg acagttggga tcgtttcttt gtcaagggcg   1140
```

-continued

| | |
|---|---|
| gtcagaaata caagtaagag ttgtttctaa aatcactgaa cttataatta gattgacaga | 1200 |
| agagtgacta accaaatggt aaaatttgat tcaggtcgcc tggtaatgct tacgtagaag | 1260 |
| gtgatgcttc tagtgctagt tatttcttgg ctggtgctgc cattactggt gaaaccgtta | 1320 |
| ctgttgaagg ttgtggaaca accagcctgc aggtaacact aagtttataa taaaatttgc | 1380 |
| ttagttcaat tttttttttgt ctttctaagg cttggctagt tgtgtcactt gtgtgtaaca | 1440 |
| tatgaagaat ctaagtttag tttttttttgg tgatgaatct caaagggaga gtgaagttc | 1500 |
| gctgaggttc ttgagaaaat gggatgtaaa gtgtcatgga cagagaacag tgtgactgtg | 1560 |
| actggaccat c | 1571 |

<210> SEQ ID NO 8
<211> LENGTH: 2270
<212> TYPE: DNA
<213> ORGANISM: Brassica napus

<400> SEQUENCE: 8

| | |
|---|---|
| atggcgcaag ctagcagaat ctgccatggc gtgcagcaga acccatgtgc tatctccaat | 60 |
| ctctccaaat caaccaccg caaatctccc ttctctgtct cgctgaagac gcaccagcag | 120 |
| cagcgtggag cttatcagat atcttcgcgg gggttgaaga agagcgcgat ggtgctaaac | 180 |
| cgttctgtaa ctcgtccggt taaggttatg gcctctgttt ccacggcgga gaaagcttcg | 240 |
| gagattgtgc ttcaacccat tagagaaatc tcgggtctga tcaagctacc cggatccaaa | 300 |
| tctctgtcca accggattct tcttcttgcc gctttatccg aggtttgctt ctttctttgt | 360 |
| ttgcttagtg ttgcgttttt aacggcgtga ggatgaagaa aggttctgac tttgttgtgg | 420 |
| ttttataggg aactactgta gttgacaact tgttgaacag tgatgacatt aactacatgc | 480 |
| ttgatgcgtt gaacaagttg gggcttaatg tggaacgtga cagtgagaac aaccgtgcgg | 540 |
| ttgttgaagg atgtggcggg atattcccag cttctttaga ttctaagggt gatatcgagt | 600 |
| tgtaccttgg gaatgcagga acagccatgc gtccacttac agctgcagtt actgctgctg | 660 |
| gtggcaacgc aaggtaaggt taaggactta ttctgttagt tagttttgat tattttaaga | 720 |
| atcggtcttg tactgatgct ttttagttgg gtttgtttac cagttatgtg cttgatgggg | 780 |
| tgcctagaat gagggaaaga cctataggag atttggttgt tggtcttaag cagcttggtg | 840 |
| ctgatgttga atgtactctt ggtactaact gtcctcctgt tcgtgtcaat gctaatggtg | 900 |
| gcctgcccgg tggaaaggtg agtttgtaat ttcagcattt gctatgtgaa agttgcagc | 960 |
| aatctttgtt catcacactg cgttagcttg acatgatttt agcttttgta tggtttcttg | 1020 |
| attgacacat tagacatgtt tttgcatttt tcaggtgaag ctttctggat caatcagtag | 1080 |
| tcaatacttg actgcactgc tcatggcagc tcccttagct cttggagacg ttgagattga | 1140 |
| gatcattgat aaattgattt ctgttccata tgttgaaatg acattgaagt tgatggaacg | 1200 |
| ttttggtgtt agtgccgagc atagtgacag ttgggatcgt ttctttgtca agggcggtca | 1260 |
| gaaatacaag taagagttgt ttctaaaatc actgaactta taattagatt gacagaagag | 1320 |
| tgactaacca aatggtaaaa tttgattcag gtcgcctggt aatgcttacg tagaaggtga | 1380 |
| tgcttctagt gctagttatt tcttggctgg tgctgccatt actggtgaaa ccgttactgt | 1440 |
| tgaaggttgt ggaacaacca gcctgcaggt aacactaagt ttataataaa atttgcttag | 1500 |
| ttcaattttt ttttgtcttt ctaaggcttg gctagttgtg tcacttgtgt gtaacatatg | 1560 |
| aagaatctaa gtttagtttt ttttggtgat gaatctcaaa gggagatgtg aagttcgctg | 1620 |

```
aggttcttga gaaaatggga tgtaaagtgt catggacaga gaacagtgtg actgtgactg    1680
gaccatctag agatgctttt ggaatgagac acttgcgtgc tgttgatgtc aacatgaaca    1740
aaatgcctga tgtagccatg actcttgccg ttgtagctct ctttgcagat ggcccaacca    1800
ccattagaga tggtaagcac accctctaat tgttttttt aaagattcat agtcacttag     1860
ttctcctctc atccattctt ttttatcata tatagtggct agctggagag taaaggagac    1920
agaaaggatg attgccattt gcacagagct taggaaggta aaacattttt ctttctgtct    1980
cgctctcact ctcactctct tggttttatg tgctcagtct aagttaagtt ctgcataact    2040
tttgcgtaca gcttggagct acagtggaag agggttcaga ttattgtgtg ataactccac    2100
cagcaaagct gaaaccggcg gagattgaca catatgatga ccatagaatg gcaatggcat    2160
tctcccttgc agcttgtgct gatgttccag tgaccatcaa agatcctggt tgtaccagga    2220
aaactttccc tgactacttc caagtccttg aaagtatcac aaagcactaa                2270
```

<210> SEQ ID NO 9
<211> LENGTH: 521
<212> TYPE: PRT
<213> ORGANISM: Brassica napus

<400> SEQUENCE: 9

```
Met Ala Gln Ala Ser Arg Ile Cys His Gly Val Gln Gln Asn Pro Cys
1               5                   10                  15

Ala Ile Ser Asn Leu Ser Lys Ser Asn His Arg Lys Ser Pro Phe Ser
            20                  25                  30

Val Ser Leu Lys Thr His Gln Gln Arg Gly Ala Tyr Gln Ile Ser
        35                  40                  45

Ser Arg Gly Leu Lys Lys Ser Ala Met Val Leu Asn Arg Ser Val Thr
    50                  55                  60

Arg Pro Val Lys Val Met Ala Ser Val Ser Thr Ala Glu Lys Ala Ser
65                  70                  75                  80

Glu Ile Val Leu Gln Pro Ile Arg Glu Ile Ser Gly Leu Ile Lys Leu
                85                  90                  95

Pro Gly Ser Lys Ser Leu Ser Asn Arg Ile Leu Leu Leu Ala Ala Leu
            100                 105                 110

Ser Glu Gly Thr Thr Val Val Asp Asn Leu Leu Asn Ser Asp Asp Ile
        115                 120                 125

Asn Tyr Met Leu Asp Ala Leu Asn Lys Leu Gly Leu Asn Val Glu Arg
    130                 135                 140

Asp Ser Glu Asn Asn Arg Ala Val Val Glu Gly Cys Gly Gly Ile Phe
145                 150                 155                 160

Pro Ala Ser Leu Asp Ser Lys Gly Asp Ile Glu Leu Tyr Leu Gly Asn
                165                 170                 175

Ala Gly Thr Ala Met Arg Pro Leu Thr Ala Ala Val Thr Ala Ala Gly
            180                 185                 190

Gly Asn Ala Ser Tyr Val Leu Asp Gly Val Pro Arg Met Arg Glu Arg
        195                 200                 205

Pro Ile Gly Asp Leu Val Val Gly Leu Lys Gln Leu Gly Ala Asp Val
    210                 215                 220

Glu Cys Thr Leu Gly Thr Asn Cys Pro Pro Val Arg Val Asn Ala Asn
225                 230                 235                 240

Gly Gly Leu Pro Gly Gly Lys Val Lys Leu Ser Gly Ser Ile Ser Ser
                245                 250                 255

Gln Tyr Leu Thr Ala Leu Leu Met Ala Ala Pro Leu Ala Leu Gly Asp
```

```
                260                 265                 270
Val Glu Ile Glu Ile Asp Lys Leu Ile Ser Val Pro Tyr Val Glu
            275                 280                 285
Met Thr Leu Lys Leu Met Glu Arg Phe Gly Val Ser Ala Glu His Ser
        290                 295                 300
Asp Ser Trp Asp Arg Phe Val Lys Gly Gln Lys Tyr Lys Ser
305                 310                 315                 320
Pro Gly Asn Ala Tyr Val Glu Gly Asp Ala Ser Ser Ser Tyr Phe
                325                 330                 335
Leu Ala Gly Ala Ala Ile Thr Gly Glu Thr Val Thr Val Gly Cys
            340                 345                 350
Gly Thr Thr Ser Leu Gln Gly Asp Val Lys Phe Ala Glu Val Leu Glu
        355                 360                 365
Lys Met Gly Cys Lys Val Ser Trp Thr Glu Asn Ser Val Thr Val Thr
    370                 375                 380
Gly Pro Ser Arg Asp Ala Phe Gly Met Arg His Leu Arg Ala Val Asp
385                 390                 395                 400
Val Asn Met Asn Lys Met Pro Asp Val Ala Met Thr Leu Ala Val Val
                405                 410                 415
Ala Leu Phe Ala Asp Gly Pro Thr Thr Ile Arg Asp Val Ala Ser Trp
            420                 425                 430
Arg Val Lys Glu Thr Glu Arg Met Ile Ala Ile Cys Thr Glu Leu Arg
        435                 440                 445
Lys Leu Gly Ala Thr Val Glu Glu Gly Ser Asp Tyr Cys Val Ile Thr
    450                 455                 460
Pro Pro Ala Lys Leu Lys Pro Ala Glu Ile Asp Thr Tyr Asp Asp His
465                 470                 475                 480
Arg Met Ala Met Ala Phe Ser Leu Ala Ala Cys Ala Asp Val Pro Val
                485                 490                 495
Thr Ile Lys Asp Pro Gly Cys Thr Arg Lys Thr Phe Pro Asp Tyr Phe
            500                 505                 510
Gln Val Leu Glu Ser Ile Thr Lys His
        515                 520

<210> SEQ ID NO 10
<211> LENGTH: 1566
<212> TYPE: DNA
<213> ORGANISM: Brassica napus

<400> SEQUENCE: 10
atggcgcaag ctagcagaat ctgccatggc gtgcagcaga acccatgtgc tatctccaat    60
ctctccaaat caaaccaccg caaatctccc ttctctgtct cgctgaagac gcaccagcag   120
cagcgtggag cttatcagat atcttcgcgg gggttgaaga gagcgcgat ggtgctaaac    180 cgttctgtaa ctcgtccggt taaggttatg gcctctgttt ccacggcgga gaaagcttcg   240
gagattgtgc ttcaacccat tagagaaatc tcgggtctga tcaagctacc cggatccaaa   300
tctctgtcca accggattct tcttcttgcc gctttatccg aggaactac tgtagttgac    360 aacttgttga cagtgatga cattaactac atgcttgatg cgttaacaa gttgggcgtt    420 aatgtggaac gtgacagtga aacaaccgt gcggttgttg aaggatgtgg cgggatattc    480
ccagcttctt tagattctaa gggtgatatc gagttgtacc ttgggaatgc aggaacagcc   540
atgcgtccac ttcagctgc agttactgct gctggtggca acgcaagtta tgtgcttgat   600
ggggtgccta gaatgaggga aagacctata ggagatttgg ttgttggtct taagcagctt   660
```

```
ggtgctgatg ttgaatgtac tcttggtact aactgtcctc ctgttcgtgt caatgctaat        720
ggtggcctgc ccggtggaaa ggtgaagctt tctggatcaa tcagtagtca atacttgact        780
gcactgctca tggcagctcc cttagctctt ggagacgttg agattgagat cattgataaa        840
ttgatttctg ttccatatgt tgaaatgaca ttgaagttga tggaacgttt tggtgttagt        900
gccgagcata gtgacagttg ggatcgtttc tttgtcaagg gcggtcagaa atacaagtcg        960
cctggtaatg cttacgtaga aggtgatgct tctagtgcta gttatttctt ggctggtgct       1020
gccattactg gtgaaaccgt tactgttgaa ggttgtggaa caaccagcct gcaggagat        1080 gtgaagttcg ctgaggttct tgagaaaatg gatgtaaag tgtcatggac agagaacagt        1140
gtgactgtga ctggaccatc tagagatgct tttggaatga gacacttgcg tgctgttgat       1200
gtcaacatga acaaaatgcc tgatgtagcc atgactcttg ccgttgtagc tctctttgca       1260
gatggcccaa ccaccattag agatgtggct agctggagag taaaggagac agaaaggatg       1320
attgccattt gcacagagct taggaagctt ggagctacag tggaagaggg ttcagattat       1380
tgtgtgataa ctccaccagc aaagctgaaa ccggcggaga ttgacacata tgatgaccat       1440
agaatggcaa tggcattctc ccttgcagct tgtgctgatg ttccagtgac catcaaagat       1500
cctggttgta ccaggaaaac tttccctgac tacttccaag tccttgaaag tatcacaaag       1560
cactaa                                                                 1566

<210> SEQ ID NO 11
<211> LENGTH: 2388
<212> TYPE: DNA
<213> ORGANISM: Brassica napus
<220> FEATURE:
<221> NAME/KEY: misc_feature
<222> LOCATION: (1035)..(1035)
<223> OTHER INFORMATION: n is a, c, g, or t

<400> SEQUENCE: 11
atggcgcaag ctagcagaat ctgccagaac ccatgtgtta tctccaatct ctccaaatca         60
aaccaacgca aatcgccctt gtctgtctcg atgaagacgc accagatatc ttcgtggggg        120
ttgaagaaga gtaacaacgg ctctgtgatt cgtccggttc gggtaacggc gtctgtttcc        180
acggctgaga atcttcgga gattgtgctt cagcccatta gagaaatctc gggtctgatc        240
aagctacccg gacccaaatc tctgtccaat cgaatccttc ttctagccgc tctatccgag        300
gtcggtttgc ttcttctt ctttgttagc ttagtgttgc gtttttaacg gcgtgagatt        360
gaagaaaggt tcacactttg ttgtggtgtt atagggaacc actgtagttg acaacttgtt        420
gaacagtgat gacatcaatt acatgcttga tgcgttgaag aaattggggc ttaatgtgga        480
acgtgacagt gagaataacc gtgcggttgt tgaaggatgt ggcgggatat tcccagcttc        540
tttagattcc aagagtgata tcgagttgta ccttgggaat gctggaacag ccatgcgtcc        600
acttaccgct gcagttactg ctgcaggtgg caacgcaagg taaggttaag gagtgtgatt        660
ttgttagtta gttttgtgtt atgtcaagaa ccgatcttgt cctcatgctt ttagttcggt        720 ttatttttcca gttatattct tggtggggtg cctagaatga gggaaaggcc tattggagat        780
ttggttgttg gtcttaagca gcttggtgct gatgttgaat gtactcttgg aactaactgc        840
cctcctgttc gcgtcaatgc taatggtggc cttcccggtg aaaggtgag tttgtaatct        900 cagcatctac tatgtggaaa gttgcaggaa ttttgttca tcacactgcg tttgctcgat        960
atgatggcct ttgtatggtt tcttgattga catattagat atgatttgca ttttcaggt       1020
```

```
gaagctatct ggttnaatca gtagtcaata cttgactgct ctgctcatgg cagctccttt    1080
agctcttgga gacgttgaga ttgagatcgt tgataaactg atctctgttc cgtatgttga    1140
aatgacattg aagttgatgg aacgttttgg tgttagtgcc gagcatagtg acagttggga    1200
tcgtttcttt gtcaagggcg gtcagaaata caagtaagcg ttgtttctga atcactgaa     1260 cttatagtta gattgacaga agagtgacta accaaatggt aaaatttgat tcaggtcgcc    1320
tggtaatgct tacgtagaag gtgatgcttc tagtgctagt tatttcttgg ctggtgccgc    1380
cattactggt gagactgtta ctgttgaagg ttgtggaaca accagcctgc aggtaacact    1440
aagtttataa tgaaatttgc ttagttcaat ttgttttttt gtctttctaa ggctttggct    1500
agttatgtgt aacatatgtt agaatctaag ctcatttttg ttgttgtgat gaatctcaaa    1560
gggagatgtg aagttcgctg aggttcttga gaaaatggga tgtaaagtgt catggacaga    1620
gaacagtgtg actgtgactg gaccatctag agatgctttt ggaatgagac acttgcgcgc    1680
tgttgatgtc aacatgaaca aaatgcctga tgtagccatg actcttgccg ttgttgctct    1740
ctttgcagat ggtccaacca ccattagaga tggtaagtac tccctctaac catctaattg    1800
aggtttttaa gattcatagt cacttagttc tcctctcatc caatcgtttt atcatatata    1860
gtggctagct ggagagtaaa ggagacagaa aggatgattg ccatttgcac agagcttagg    1920
aaggtaaaac aattttcttt ctgtcccgct ctcactctct tggttttatg tgctcagtct    1980 aggtaagtt ctgcataact tttgcgtgca gcttggagct acagtggaag agggttcaga     2040
ttattgtgtg ataactccac cagcaaagct gaaaccggcg gagattgaca catatgatga    2100
tcatagaatg gcaatggcat tctcccttgc agcttgtgct gatgttccag taaccatcaa    2160
agatcctggt tgcaccagga aaactttccc tgactacttc caggtccttg aaagtatcac    2220
aaagcactaa acagaccta aagcccattt gtcttttctt tttgatccaa ttgggatcag     2280
tttcctctgt tatcactgta agattacgaa aaacaaagag tattaagatt gtttgcttgt    2340
accttaaact gtttgatgca atcgttgaat cagttttggg ccaagggc                 2388
```

<210> SEQ ID NO 12
<211> LENGTH: 510
<212> TYPE: PRT
<213> ORGANISM: Brassica napus
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (508)..(508)
<223> OTHER INFORMATION: Xaa can be any naturally occurring amino acid

<400> SEQUENCE: 12

```
Met Ala Gln Ala Ser Arg Ile Cys Gln Asn Pro Cys Val Ile Ser Asn
1               5                   10                  15

Leu Ser Lys Ser Asn Gln Arg Lys Ser Pro Leu Ser Val Ser Met Lys
            20                  25                  30

Thr His Gln Ile Ser Ser Trp Gly Leu Lys Lys Ser Asn Asn Gly Ser
        35                  40                  45

Val Ile Arg Pro Val Arg Val Thr Ala Ser Val Ser Thr Ala Glu Lys
    50                  55                  60

Ser Ser Glu Ile Val Leu Gln Pro Ile Arg Glu Ile Ser Gly Leu Ile
65                  70                  75                  80

Lys Leu Pro Gly Pro Lys Ser Leu Ser Asn Arg Ile Leu Leu Leu Ala
            85                  90                  95
```

```
Ala Leu Ser Glu Gly Thr Thr Val Val Asp Asn Leu Leu Asn Ser Asp
            100                 105                 110

Asp Ile Asn Tyr Met Leu Asp Ala Leu Lys Lys Leu Gly Leu Asn Val
            115                 120                 125

Glu Arg Asp Ser Glu Asn Asn Arg Ala Val Val Glu Gly Cys Gly Gly
            130                 135                 140

Ile Phe Pro Ala Ser Leu Asp Ser Lys Ser Asp Ile Glu Leu Tyr Leu
145                 150                 155                 160

Gly Asn Ala Gly Thr Ala Met Arg Pro Leu Thr Ala Ala Val Thr Ala
            165                 170                 175

Ala Gly Gly Asn Ala Ser Tyr Ile Leu Gly Gly Val Pro Arg Met Arg
            180                 185                 190

Glu Arg Pro Ile Gly Asp Leu Val Val Gly Leu Lys Gln Leu Gly Ala
            195                 200                 205

Asp Val Glu Cys Thr Leu Gly Thr Asn Cys Pro Pro Val Arg Val Asn
            210                 215                 220

Ala Asn Gly Gly Leu Pro Gly Gly Lys Val Lys Leu Ser Gly Xaa Ile
225                 230                 235                 240

Ser Ser Gln Tyr Leu Thr Ala Leu Leu Met Ala Ala Pro Leu Ala Leu
            245                 250                 255

Gly Asp Val Glu Ile Glu Ile Val Asp Lys Leu Ile Ser Val Pro Tyr
            260                 265                 270

Val Glu Met Thr Leu Lys Leu Met Glu Arg Phe Gly Val Ser Ala Glu
            275                 280                 285

His Ser Asp Ser Trp Asp Arg Phe Phe Val Lys Gly Gly Gln Lys Tyr
            290                 295                 300

Lys Ser Pro Gly Asn Ala Tyr Val Glu Gly Asp Ala Ser Ser Ala Ser
305                 310                 315                 320

Tyr Phe Leu Ala Gly Ala Ala Ile Thr Gly Glu Thr Val Thr Val Glu
            325                 330                 335

Gly Cys Gly Thr Thr Ser Leu Gln Gly Asp Val Lys Phe Ala Glu Val
            340                 345                 350

Leu Glu Lys Met Gly Cys Lys Val Ser Trp Thr Glu Asn Ser Val Thr
            355                 360                 365

Val Thr Gly Pro Ser Arg Asp Ala Phe Gly Met Arg His Leu Arg Ala
            370                 375                 380

Val Asp Val Asn Met Asn Lys Met Pro Asp Val Ala Met Thr Leu Ala
385                 390                 395                 400

Val Val Ala Leu Phe Ala Asp Gly Pro Thr Thr Ile Arg Asp Val Ala
            405                 410                 415

Ser Trp Arg Val Lys Glu Thr Glu Arg Met Ile Ala Ile Cys Thr Glu
            420                 425                 430

Leu Arg Lys Leu Gly Ala Thr Val Glu Glu Gly Ser Asp Tyr Cys Val
            435                 440                 445

Ile Thr Pro Pro Ala Lys Leu Lys Pro Ala Glu Ile Asp Thr Tyr Asp
            450                 455                 460

Asp His Arg Met Ala Met Ala Phe Ser Leu Ala Ala Cys Ala Asp Val
465                 470                 475                 480

Pro Val Thr Ile Lys Asp Pro Gly Cys Thr Arg Lys Thr Phe Pro Asp
            485                 490                 495

Tyr Phe Gln Val Leu Glu Ser Ile Thr Lys His Xaa Thr Asp
            500                 505                 510
```

<210> SEQ ID NO 13
<211> LENGTH: 1530
<212> TYPE: DNA
<213> ORGANISM: Brassica napus
<220> FEATURE:
<221> NAME/KEY: misc_feature
<222> LOCATION: (716)..(716)
<223> OTHER INFORMATION: n is a, c, g, or t

<400> SEQUENCE: 13

```
atggcgcaag ctagcagaat ctgccagaac ccatgtgtta tctccaatct ctccaaatca      60
aaccaacgca aatcgccctt gtctgtctcg atgaagacgc accagatatc ttcgtggggg     120
ttgaagaaga gtaacaacgg ctctgtgatt cgtccggttc gggtaacggc gtctgtttcc     180
acggctgaga atcttcgga gattgtgctt cagcccatta gagaaatctc gggtctgatc      240
aagctacccg acccaaatc tctgtccaat cgaatccttc ttctagccgc tctatccgag      300
ggaaccactg tagttgacaa cttgttgaac agtgatgaca tcaattacat gcttgatgcg     360
ttgaagaaat tggggcttaa tgtggaacgt gacagtgaga ataaccgtgc ggttgttgaa     420
ggatgtggcg ggatattccc agcttcttta gattccaaga gtgatatcga gttgtacctt     480
gggaatgctg aacagccat gcgtccactt accgctgcag ttactgctgc aggtggcaac      540
gcaagttata ttcttggtgg ggtgcctaga atgagggaaa ggcctattgg agatttggtt     600
gttggtctta agcagcttgg tgctgatgtt gaatgtactc ttggaactaa ctgccctcct     660
gttcgcgtca atgctaatgg tggccttccc ggtggaaagg tgaagctatc tggttnaatc     720
agtagtcaat acttgactgc tctgctcatg gcagctcctt agctcttgg agacgttgag     780
attgagatcg ttgataaact gatctctgtt ccgtatgttg aaatgacatt gaagttgatg     840
gaacgttttg tgttagtgc cgagcatagt gacagttggg atcgtttctt tgtcaagggc     900
ggtcagaaat acaagtcgcc tggtaatgct tacgtagaag gtgatgcttc tagtgctagt     960
tatttcttgg ctggtgccgc cattactggt gagactgtta ctgttgaagg ttgtggaaca    1020
accagcctgc agggagatgt gaagttcgct gaggttcttg agaaaatggg atgtaaagtg    1080
tcatggacag agaacagtgt gactgtgact ggaccatcta gagatgcttt tggaatgaga    1140
cacttgcgcg ctgttgatgt caacatgaac aaaatgcctg atgtagccat gactcttgcc    1200
gttgttgctc tctttgcaga tggtccaacc accattagag atgtggctag ctggagagta    1260
aaggagacag aaaggatgat tgccattttgc acagagctta ggaagcttgg agctacagtg    1320
gaagagggtt cagattattg tgtgataact ccaccagcaa agctgaaacc ggcggagatt    1380
gacacatatg atgatcatag aatggcaatg gcattctccc ttgcagcttg tgctgatgtt    1440
ccagtaacca tcaaagatcc tggttgcacc aggaaaactt tccctgacta cttccaggtc    1500
cttgaaagta tcacaaagca ctaaacagac                                    1530
```

<210> SEQ ID NO 14
<211> LENGTH: 2834
<212> TYPE: DNA
<213> ORGANISM: Brassica napus

<400> SEQUENCE: 14

```
atggcgcaag ctagcagaat ctgccatggc gtgcagaacc catgtgttat catctccaat      60
ctctccaaat caaaccaaaa caaatcacct ttctccgtct cgctgaagac gcagcagtct     120
cgagcttctt cgtggggact aaagaagagt ggaacgatgc taaacggttc tgtaattcgc     180
ccggttaagg taacagcttc cgtttccacg gccgagaaag cttcagagat tgtgcttcaa     240
```

```
ccaattagag aaatctcggg tctcattaag ctacccggat ccaaatctct ctccaatcgg    300
atcctccttc ttgctgctct atctgaggta catatacttg attagtgtta ggcctttgct    360
gtgagatttt gggaactata gacaatttag taagaattta tatattattt ttaaaaaatt    420
aaaagcctat atatatatat atttaaaatt ttcaaaaaat tatggaggtt tgagactgaa    480
gaaagttttt ttttaattat tattataggg aactactgta gtggacaact tgttgaacag    540
tgatgacatc aactacatgc ttgatgcgtt gaagaagctg gggcttaacg tggaacgtga    600
cagggtaaac aaccgtgctg tagttgaagg atgtggtgga atattcccag cttccttaga    660
ttccaagagt gatattgagt tgtaccttgg gaatgcagga acagccatgc gtccactcac    720
cgctgccgtt actgctgcag gtggcaacgc aaggtaaagg ttaaggagct ttttgttatt    780
gtcaagaaat tgattttgtg tttgatgctt ttagtttggt ttgttttcta gttatgtgct    840
tgatggggtg cctagaatga gggagagacc tataggagat ttggttgttg gtcttaagca    900
gcttggtgct gatgttgaat gtactctcgg cactaactgt cctcctgttc gtgtcaatgc    960
taatggtggc cttcccggtg aaaggtgat cttgtttgca gcagtctttg ttcatcacag   1020
cctttgcttc acattattac atcttttagt ttgttgttgt gacttgatgg atcttaaaaa   1080
aaggaattgg gaactggtgt gaaagtgatt agcaatcttt ctcgattcct tgcagggccg   1140
tgggcattac taagtgaaac attagcctat taacccccaa atattttgaa aaaaatttag   1200
tatatggccc caaaatagtt tttaagaaat tagaaaaact tttaataaat cgtctacggt   1260
ccccatttta gagccgaccc tgcttgtatg gtttcttgag tgagatattt tacatgtttt   1320
gcattttcag gtgaagcttt ctggatcaat cagtagtcaa tacttgactg ccttgctcat   1380
ggcagctcct ttagctcttg gagacgtgga gattgagatc attgataaac tgatttctgt   1440
tccatatgtt gaaatgacat tgaagttgat ggaacgtttt ggtgttagtg ccgagcatag   1500
tgatagctgg gatcgtttct ttgtcaaggg cggtcagaag tacaagtaag aattctttaa   1560
attaaagaat tagattgaag aaaatgactg attaaccaaa tggcaaaact gattcaggtc   1620
gcctggtaat gcttatgtag aaggtgatgc ttctagtgct agctacttct tggctggtgc   1680
tgctattacc ggtgaaaccg tcactgttga aggttgtgga acaactagcc tccaggtagt   1740
ttctccactc tgaatcatca aatattatac tccctccgtt ttgtattaag tgtcattttta   1800 gcttttaaat tttgtctcat taaaagtgtc attttacatt ttcaatgtat atattaaata   1860
aattttccag ttttttactaa ttcattatat taaataatat aaaacagaaa atttaacaat   1920
tatcgtaatt cgtgtgcaaa gttgattagt tcaaagttgt gtgtaacatg ttttgaagaa   1980
tctaagctca ttctcttttt attttttttg tgatgaatcc caaagggaga tgtgaaattc   2040
gcagaggtac ttgagaaaat gggatgtaaa gtgtcatgga cagagaacag tgtgactgtg   2100
actggaccat ctagagatgc ttttggaatg agacacttgc gtgctgttga tgtcaacatg   2160
aataaaatgc ccgatgtagc catgactctt gccgttgttg ctctctttgc cgatggtcca   2220
accaccatca gagatggtaa agcaaaaccc tctctttgaa tcagcgtctt ttaaaagatt   2280
catggttgct ttaactctat ttggtcaatg tagtggctag ctggagagtt aaggagacag   2340
aaaggatgat agccatctgc acagagcttc gaaaggtaag tttccttttc tctcatgctc   2400
tcattctaag ttaatcgttg cataacttttt tggggttttt ttttgcgtt cagcttggag   2460 ctacagtgga agaaggttca gattattgtg tgataactcc accagcgaag gtgaaaccgg   2520
cggagattga tacgtatgat gatcatagaa tggcgatggc gttctcgctt gcagcatgtg   2580
```

-continued

```
ctgatgttcc agtcaccatc aaggatcctg gctgcaccag aaagactttc cctgactact    2640
ttcaagtcct tgaaagtatc acaaagcact aaaaagatca tttcctttga atccaaatgt    2700
gagaatgtgt tcttcctct  ctctgttgcc actgtaacat ttattagaag aacaaagtgt    2760
gtgtgtttaa gagtgtgttt gcttgtaatg aactgagtga gatgcaatcg ttgaatcagt    2820
tttgggccaa gggc                                                      2834

<210> SEQ ID NO 15
<211> LENGTH: 516
<212> TYPE: PRT
<213> ORGANISM: Brassica napus

<400> SEQUENCE: 15

Met Ala Gln Ala Ser Arg Ile Cys His Gly Val Gln Asn Pro Cys Val
1               5                   10                  15

Ile Ile Ser Asn Leu Ser Lys Ser Asn Gln Asn Lys Ser Pro Phe Ser
                20                  25                  30

Val Ser Leu Lys Thr Gln Gln Ser Arg Ala Ser Ser Trp Gly Leu Lys
            35                  40                  45

Lys Ser Gly Thr Met Leu Asn Gly Ser Val Ile Arg Pro Val Lys Val
        50                  55                  60

Thr Ala Ser Val Ser Thr Ala Glu Lys Ala Ser Glu Ile Val Leu Gln
65                  70                  75                  80

Pro Ile Arg Glu Ile Ser Gly Leu Ile Lys Leu Pro Gly Ser Lys Ser
                85                  90                  95

Leu Ser Asn Arg Ile Leu Leu Leu Ala Ala Leu Ser Glu Gly Thr Thr
            100                 105                 110

Val Val Asp Asn Leu Leu Asn Ser Asp Asp Ile Asn Tyr Met Leu Asp
        115                 120                 125

Ala Leu Lys Lys Leu Gly Leu Asn Val Glu Arg Asp Arg Val Asn Asn
    130                 135                 140

Arg Ala Val Val Glu Gly Cys Gly Gly Ile Phe Pro Ala Ser Leu Asp
145                 150                 155                 160

Ser Lys Ser Asp Ile Glu Leu Tyr Leu Gly Asn Ala Gly Thr Ala Met
                165                 170                 175

Arg Pro Leu Thr Ala Ala Val Thr Ala Ala Gly Gly Asn Ala Ser Tyr
            180                 185                 190

Val Leu Asp Gly Val Pro Arg Met Arg Glu Arg Pro Ile Gly Asp Leu
        195                 200                 205

Val Val Gly Leu Lys Gln Leu Gly Ala Asp Val Glu Cys Thr Leu Gly
    210                 215                 220

Thr Asn Cys Pro Pro Val Arg Val Asn Ala Asn Gly Gly Leu Pro Gly
225                 230                 235                 240

Gly Lys Val Lys Leu Ser Gly Ser Ile Ser Ser Gln Tyr Leu Thr Ala
                245                 250                 255

Leu Leu Met Ala Ala Pro Leu Ala Leu Gly Asp Val Glu Ile Glu Ile
            260                 265                 270

Ile Asp Lys Leu Ile Ser Val Pro Tyr Val Glu Met Thr Leu Lys Leu
        275                 280                 285

Met Glu Arg Phe Gly Val Ser Ala Glu His Ser Asp Ser Trp Asp Arg
    290                 295                 300

Phe Phe Val Lys Gly Gly Gln Lys Tyr Lys Ser Pro Gly Asn Ala Tyr
305                 310                 315                 320

Val Glu Gly Asp Ala Ser Ser Ala Ser Tyr Phe Leu Ala Gly Ala Ala
```

```
            325                 330                 335
Ile Thr Gly Glu Thr Val Thr Val Glu Gly Cys Gly Thr Thr Ser Leu
        340                 345                 350
Gln Gly Asp Val Lys Phe Ala Glu Val Leu Glu Lys Met Gly Cys Lys
        355                 360                 365
Val Ser Trp Thr Glu Asn Ser Val Thr Val Thr Gly Pro Ser Arg Asp
        370                 375                 380
Ala Phe Gly Met Arg His Leu Arg Ala Val Asp Val Asn Met Asn Lys
385                 390                 395                 400
Met Pro Asp Val Ala Met Thr Leu Ala Val Ala Leu Phe Ala Asp
                405                 410                 415
Gly Pro Thr Thr Ile Arg Asp Val Ala Ser Trp Arg Val Lys Glu Thr
                420                 425                 430
Glu Arg Met Ile Ala Ile Cys Thr Glu Leu Arg Lys Leu Gly Ala Thr
                435                 440                 445
Val Glu Glu Gly Ser Asp Tyr Cys Val Ile Thr Pro Pro Ala Lys Val
        450                 455                 460
Lys Pro Ala Glu Ile Asp Thr Tyr Asp Asp His Arg Met Ala Met Ala
465                 470                 475                 480
Phe Ser Leu Ala Ala Cys Ala Asp Val Pro Val Thr Ile Lys Asp Pro
                485                 490                 495
Gly Cys Thr Arg Lys Thr Phe Pro Asp Tyr Phe Gln Val Leu Glu Ser
                500                 505                 510
Ile Thr Lys His
        515

<210> SEQ ID NO 16
<211> LENGTH: 1554
<212> TYPE: DNA
<213> ORGANISM: Brassica napus

<400> SEQUENCE: 16
atggcgcaag ctagcagaat ctgccatggc gtgcagaacc catgtgttat catctccaat      60
ctctccaaat caaaccaaaa caaatcacct ttctccgtct cgctgaagac gcagcagtct     120
cgagcttctt cgtggggact aaagaagagt ggaacgatgc taaacggttc tgtaattcgc     180
ccggttaagg taacagcttc cgtttccacg gccgagaaag cttcagagat tgtgcttcaa     240
ccaattagag aaatctcggg tctcattaag ctacccggat ccaaatctct ctccaatcgg     300
atcctccttc ttgctgctct atctgaggga actactgtag tggacaactt gttgaacagt     360
gatgacatca actacatgct tgatgcgttg aagaagctgg ggcttaacgt ggaacgtgac     420
agggtaaaca accgtgctgt agttgaagga tgtggtggaa tattcccagc ttccttagat     480
tccaagagtg atattgagtt gtaccttggg aatgcaggaa cagccatgcg tccactcacc     540
gctgccgtta ctgctgcagg tggcaacgca agttatgtgc ttgatggggt gcctagaatg     600
agggagagac ctataggaga tttggttgtt ggtcttaagc agcttggtgc tgatgttgaa     660
tgtactctcg gcactaactg tcctcctgtt cgtgtcaatg ctaatggtgg ccttcccggt     720
ggaaaggtga agctttctgg atcaatcagt agtcaatact tgactgcctt gctcatggca     780
gctcctttag ctcttggaga cgtggagatt gagatcattg ataaactgat ttctgttcca     840
tatgttgaaa tgacattgaa gttgatggaa cgttttggtg ttagtgccga gcatagtgat     900
agctgggatc gtttctttgt caagggcggt cagaagtaca agtcgcctgg taatgcttat     960
gtagaaggtg atgcttctag tgctagctac ttcttggctg gtgctgctat taccggtgaa    1020
```

```
accgtcactg ttgaaggttg tggaacaact agcctccagg gagatgtgaa attcgcagag    1080
gtacttgaga aaatgggatg taaagtgtca tggacagaga acagtgtgac tgtgactgga    1140
ccatctagag atgcttttgg aatgagacac ttgcgtgctg ttgatgtcaa catgaataaa    1200
atgcccgatg tagccatgac tcttgccgtt gttgctctct tgccgatgg tccaaccacc     1260 atcagagatg tggctagctg gagagttaag gagacagaaa ggatgatagc catctgcaca    1320
gagcttcgaa agcttggagc tacagtgaa gaaggttcag attattgtgt gataactcca     1380
ccagcgaagg tgaaaccggc ggagattgat acgtatgatg atcatagaat ggcgatggcg    1440
ttctcgcttg cagcatgtgc tgatgttcca gtcaccatca aggatcctgg ctgcaccaga    1500
aagactttcc ctgactactt tcaagtcctt gaaagtatca caaagcacta aaaa         1554
```

<210> SEQ ID NO 17
<211> LENGTH: 2958
<212> TYPE: DNA
<213> ORGANISM: Brassica napus

<400> SEQUENCE: 17

```
atggcgcaag ctagcagaat ctgccatggc gtgcagaacc catgtgttat catctccaat      60
ctctccaaat ccaaccaaaa caaatcacct ttctccgtct ccttgaagac gcatcagcct     120
cgagcttctt cgtggggatt gaagaagagt ggaacgatgc taaacggttc tgtaattcgc     180
ccggttaagg taacagcttc tgtttccacg tccgagaaag cttcagagat tgtgcttcaa     240 ccaatcgag aaatctcggg tctcattaag ctacccggat ccaaatctct ctccaatcgg      300
atcctccttc ttgccgctct atctgaggta catatacttg cttagtgtta ggcctttgct     360
gtgagatttt gggaactata gacaatttag taagaattta tatataattt ttttaaaaaa    420
aatcagaagc ctatatatat ttaaatttt ccaaaattt tggaggttat aggcttatgt      480
tacaccattc tagtctgcat cttcggtt gagactgaag aatttatt tttaaaaaat        540 tattataggg aactactgta gtggacaact tgttgaacag tgatgacatc aactacatgc     600
ttgatgcgtt gaagaagctg gggcttaacg tggaacgtga cagtgtaaac aaccgtgcgg    660
ttgttgaagg atgcggtgga atattcccag cttccttaga ttccaagagt gatattgagt    720
tgtaccttgg gaatgcagga acagccatgc gtccactcac cgctgcagtt acagctgcag    780
gtggcaacgc gaggtaaggt taacgagttt tttgttattg tcaagaaatt gatcttgtgt    840
ttgatgcttt tagtttggtt tgttttctag tgatgtactt gatggggtgc ctagaatgag    900
ggaaagacct ataggagatt tggttgttgg tcttaagcag cttggtgctg atgttgagtg    960
tactcttggc actaactgtc ctcctgttcg tgtcaatgct aatggtggcc ttcccggtgg   1020
gaaggtgatc ttcacattta ctctatgaat tgtttgcagc agtctttgtt catcacagcc    1080
tttgcttcac attatttcat cttttagttt gttgttatat tacttgatgg atctttaaaa    1140
aggaattggg tctggtgtga agtgattag caatctttct cgattccttg cagggccgtg     1200
ggcattacta agtgaaacat tagcctatta acccccaaaa ttttgaaaa aaattagta      1260 tatggcccca aaatagtttt taaaaaatta gaaaaacttt taataaatcg tctacagtcc    1320 caaaatctt agagccggcc ctgcttgtat ggtttctcga ttgatatatt agactatgtt      1380 ttgaatttc aggtgaagct tcctggatcg atcagtagtc agtacttgac tgccctcctc    1440
atggcagctc ctttagctct tggagacgtg gagattgaga tcattgataa actgatatct    1500
gttccatatg ttgaaatgac attgaagttg atggagcgtt ttggtgttag tgccgagcat   1560
```

```
agtgatagct gggatcgttt ctttgtcaag ggcggtcaga aatacaagta atgagttctt    1620
ttaagttgag agttagattg aagaatgaat gactgattaa ccaaatggca aaactgattc    1680
aggtcgcctg gtaatgctta tgtagaaggt gatgcttcta gtgctagcta cttcttggct    1740
ggtgctgcca ttactggtga aactgttact gtcgaaggtt gtggaacaac tagcctccag    1800
gtagtttatc cactctgaat catcaaatat tatactccct ccgttttatg ttaagtgtca    1860
ttagctttta aattttgttt cattaaaagt gtcattttac attttcaatg catatattaa    1920
ataaatttc cagttttac taattcatta attagcaaaa tcaaacaaaa attatattaa     1980
ataatgtaaa attcgtaatt tgtgtgcaaa taccttaaac cttatgaaac ggaaacctta    2040
tgaaacagag ggagtactaa ttttataata aaatttgatt agttcaaagt tgtgtataac    2100
atgttctgta agaatctaag ctcattctct tttattttt tgtgatgaat cccaaaggga    2160
gatgtgaaat tcgcagaggt tcttgagaaa atgggatgta aggtgtcatg gacagagaac    2220
agtgtgactg tgactggacc atcaagagat gcttttggaa tgaggcactt gcgtgctgtt    2280
gatgtcaaca tgaacaaaat gcctgatgta gccatgactc tagccgttgt tgctctcttt    2340
gccgatggtc caaccaccat cagagatggt aaagcaaaac cctctctttg aatcagcgtg    2400
ttttaaaaga ttcatggttg cttaaactct atttggtcaa tgtagtggct agctggagag    2460
ttaaggagac agagaggatg attgccattt gcacagagct tagaaaggta agtttccttt    2520
tctctcatgc tctctcattc gaagttaatc gttgcataac ttttgcggt tttttttttt    2580
gcgttcagct tggagctaca gtggaagaag gttcagatta ttgtgtgata actccaccag    2640
caaaggtgaa accggcggag attgatacgt atgatgatca tagaatggcg atggcgttct    2700
cgcttgcagc ttgtgctgat gttccagtca ccatcaagga tcctggctgc accaggaaga    2760
ctttccctga ctacttccaa gtccttgaaa gtatcacaaa gcattaaaag acccttccct    2820
ctgatccaaa tgtgagaatc tgttgctttc tctttgttgc caccgtaaca tttattagaa    2880
gaacaaagtg tgtgtgttaa gagtgtgttt gcttgtaatg aactgagtga gatgcaatcg    2940
ttgaatcagt tttgggcc                                                 2958
```

<210> SEQ ID NO 18
<211> LENGTH: 515
<212> TYPE: PRT
<213> ORGANISM: Brassica napus

<400> SEQUENCE: 18

```
Met Ala Gln Ser Ser Arg Ile Cys His Gly Val Gln Asn Pro Cys Val
1               5                   10                  15

Ile Ile Ser Asn Leu Ser Lys Ser Asn Gln Asn Lys Ser Pro Phe Ser
            20                  25                  30

Val Ser Leu Lys Thr His Gln Pro Arg Ala Ser Ser Trp Gly Leu Lys
        35                  40                  45

Lys Ser Gly Thr Met Leu Asn Gly Ser Val Ile Arg Pro Val Lys Val
    50                  55                  60

Thr Ala Ser Val Ser Thr Ser Glu Lys Ala Ser Glu Ile Val Leu Gln
65                  70                  75                  80

Pro Ile Arg Glu Ile Ser Gly Leu Ile Lys Leu Pro Gly Ser Lys Ser
                85                  90                  95

Leu Ser Asn Arg Ile Leu Leu Leu Ala Ala Leu Ser Glu Gly Thr Thr
            100                 105                 110

Val Val Asp Asn Leu Leu Asn Ser Asp Asp Ile Asn Tyr Met Leu Asp
        115                 120                 125
```

Ala Leu Lys Lys Leu Gly Leu Asn Val Glu Arg Asp Ser Val Asn Asn
130                 135                 140

Arg Ala Val Val Glu Gly Cys Gly Gly Ile Phe Pro Ala Ser Leu Asp
145                 150                 155                 160

Ser Lys Ser Asp Ile Glu Leu Tyr Leu Gly Asn Ala Gly Thr Ala Met
            165                 170                 175

Arg Pro Leu Thr Ala Ala Val Thr Ala Ala Gly Gly Asn Ala Ser Tyr
            180                 185                 190

Val Leu Asp Gly Val Pro Arg Met Arg Glu Arg Pro Ile Gly Asp Leu
            195                 200                 205

Val Val Gly Leu Lys Gln Leu Gly Ala Asp Val Glu Cys Thr Leu Gly
210                 215                 220

Thr Asn Cys Pro Pro Val Arg Val Asn Ala Asn Gly Gly Leu Pro Gly
225                 230                 235                 240

Gly Lys Val Lys Leu Ser Gly Ser Ile Ser Ser Gln Tyr Leu Thr Ala
            245                 250                 255

Leu Leu Met Ala Ala Pro Leu Ala Leu Gly Asp Val Glu Ile Glu Ile
            260                 265                 270

Ile Asp Lys Leu Ile Ser Val Pro Tyr Val Glu Met Thr Leu Lys Leu
            275                 280                 285

Met Glu Arg Phe Gly Val Ser Ala Glu His Ser Asp Ser Trp Asp Arg
290                 295                 300

Phe Phe Val Lys Gly Gly Gln Lys Tyr Lys Ser Pro Gly Asn Ala Tyr
305                 310                 315                 320

Val Glu Gly Asp Ala Ser Ser Ala Ser Tyr Phe Leu Ala Gly Ala Ala
            325                 330                 335

Ile Thr Gly Glu Thr Val Thr Val Glu Gly Cys Gly Thr Thr Ser Leu
            340                 345                 350

Gln Gly Asp Val Lys Phe Ala Glu Val Leu Glu Lys Met Gly Cys Lys
            355                 360                 365

Val Ser Trp Thr Glu Asn Ser Val Thr Val Thr Gly Pro Ser Arg Asp
370                 375                 380

Ala Phe Gly Met Arg His Leu Arg Ala Val Asp Val Asn Met Asn Lys
385                 390                 395                 400

Met Pro Asp Val Ala Met Thr Leu Ala Val Val Ala Leu Phe Ala Asp
            405                 410                 415

Gly Pro Thr Thr Ile Arg Asp Val Ala Ser Trp Arg Val Lys Glu Thr
            420                 425                 430

Glu Arg Met Ile Ala Ile Cys Thr Glu Leu Arg Lys Leu Gly Ala Thr
            435                 440                 445

Val Glu Glu Gly Ser Asp Tyr Cys Val Ile Thr Pro Pro Ala Lys Val
450                 455                 460

Lys Pro Ala Glu Ile Asp Thr Tyr Asp Asp His Arg Met Ala Met Ala
465                 470                 475                 480

Phe Ser Leu Ala Ala Cys Ala Asp Val Pro Val Thr Ile Lys Asp Pro
            485                 490                 495

Gly Cys Thr Arg Lys Thr Phe Pro Asp Tyr Phe Gln Val Leu Glu Ser
            500                 505                 510

Ile Thr Lys
515

<210> SEQ ID NO 19
<211> LENGTH: 1547

```
<212> TYPE: DNA
<213> ORGANISM: Brassica napus

<400> SEQUENCE: 19
atggcgcaat ctagcagaat ctgccatggc gtgcagaacc catgtgttat catctccaat       60
ctctccaaat ccaaccaaaa caaatcacct ttctccgtct ccttgaagac gcatcagcct      120
cgagcttctt cgtggggatt gaagaagagt ggaacgatgc taaacggttc tgtaattcgc      180
ccggttaagg taacagcttc tgtttccacg tccgagaaag cttcagagat tgtgcttcaa      240
ccaatcagag aaatctcggg tctcattaag ctacccggat ccaaatctct ctccaatcgg      300
atcctccttc ttgccgctct atctgaggga actactgtag tggacaactt gttgaacagt      360
gatgacatca actacatgct tgatgcgttg aagaagctgg ggcttaacgt ggaacgtgac      420
agtgtaaaca accgtgcggt tgttgaagga tgcggtggaa tattcccagc ttccttagat      480
tccaagagtg atattgagtt gtaccttggg aatgcaggaa cagccatgcg tccactcacc      540
gctgcagtta cagctgcagg tggcaacgcg agttatgtac ttgatggggt gcctagaatg      600
agggaaagac ctataggaga tttggttgtt ggtcttaagc agcttggtgc tgatgttgag      660
tgtactcttg gcactaactg tcctcctgtt cgtgtcaatg ctaatggtgg ccttcccggt      720
ggaaaggtga agctttctgg atcgatcagt agtcagtact tgactgccct cctcatggca      780
gctcctttag ctcttggaga cgtggagatt gagatcattg ataaactgat atctgttcca      840
tatgttgaaa tgacattgaa gttgatggag cgttttggtg ttagtgccga gcatagtgat      900
agctgggatc gtttctttgt caagggcggt cagaaataca agtcgcctgg taatgcttat      960
gtagaaggtg atgcttctag tgctagctac ttcttggctg gtgctgccat tactggtgaa     1020
actgttactg tcgaaggttg tggaacaact agcctccagg gagatgtgaa attcgcagag     1080
gttcttgaga aaatgggatg taaagtgtca tggacagaga acagtgtgac tgtgactgga     1140
ccatcaagag atgcttttgg aatgaggcac ttgcgtgctg ttgatgtcaa catgaacaaa     1200
atgcctgatg tagccatgac tctagccgtt gttgctctct tgccgatggg tccaaccacc     1260
atcagagatg tggctagctg gagagttaag gagacagaga ggatgattgc catttgcaca     1320
gagcttagaa agcttggagc tacagtggaa gaaggttcag attattgtgt gataactcca     1380
ccagcaaagg tgaaaccggc ggagattgat acgtatgatg atcatagaat ggcgatggcg     1440
ttctcgcttg cagcttgtgc tgatgttcca gtcaccatca aggatcctgg ctgcaccagg     1500
aagactttcc ctgactactt ccaagtcctt gaaagtatca caaagca                   1547

<210> SEQ ID NO 20
<211> LENGTH: 4888
<212> TYPE: DNA
<213> ORGANISM: Artificial Sequence
<220> FEATURE:
<223> OTHER INFORMATION: Expression cassette from pDAB100331

<400> SEQUENCE: 20
gagcataatt tttattaatg tactaaatta ctgttttgtt aaatgcaatt ttgctttctc       60
gggatttttaa tatcaaaatc tatttagaaa tacacaatat tttgttgcag gcttgctgga      120
gaatcgatct gctatcataa aaattacaaa aaaatttat ttgcctcaat tattttagga       180
ttggtattaa ggacgcttaa attatttgtc gggtcactac gcatcattgt gattgagaag      240
atcagcgata cgaaatattc gtagtactat cgcgataatt tatttgaaaa ttcatatgaa      300
aagcaaacgt tacatgaatt gatgaaacaa tacaaagaca gataaagcca cgcacattta      360
```

```
ggatattggc cgagattact gaatattgag taagatcacg gaatttctga caggagcatg      420
tcttcaattc agcccaaatg gcagttgaaa tactcaaacc gccccatatg caggagcgga      480
tcattcattg tttgtttggt tgcctttgcc aacatgggag tccaaggttt ggtgacctcg      540
aggcttaaga ctttactaaa acttcaaaag aaaaacaata taaaaacgat aatccaaatg      600
cattattgat ctatataaca tcaagacaaa aatacatatg tgactcttat tcaggtctta      660
ggtttattac agcaaagatc atgacttgat cacttcaaac aaagtacgta actataaaaa      720
cgagtcaaat agattgtctt acactaacgt gtcgatagaa taatttgacc aaaaggtgat      780
cttattacag aaatagccac tgagctcggt agcaattccc gaggctgtag ccgacgatgg      840
tgcgccagga gagttgttga ttcattgttt gcctccctgc tgcggttttt caccgaagtt      900
catgccagtc cagcgttttt gcagcagaaa agccgccgac ttcggtttgc ggtcgcgagt      960
gaagatccct ttcttgttac cgccaacgcg caatatgcct tgcgaggtcg caaaatcggc     1020
gaaattccat acctgttcac cgacgacggc gctgacgcga tcaaagacgc ggtgatacat     1080
atccagccat gcacactgat actcttcact ccacatgtcg gtgtacattg agtgcagccc     1140
ggctaacgta tccacgccgt attcggtgat gataatcggc tgatgcagtt ctcctgcca      1200 ggccagaagt tcttttttcca gtaccttctc tgccgttttcc aaatcgccgc tttggacata     1260
ccatccgtaa taacggttca ggcacagcac atcaaagaga tcgctgatgg tatcggtgtg     1320
agcgtcgcag aacattacat tgacgcaggt gatcggacgc gtcgggtcga gtttacgcgt     1380
tgcttccgcc agtggcgcga aatattcccg tgcaccttgc ggacgggtat ccggttcgtt     1440
ggcaatactc cacatcacca cgcttgggtg gttttttgtca cgcgctatca gctctttaat     1500
cgcctgtaag tgcgcttgct gagtttcccc gttgactgcc tcttcgctgt acagttcttt     1560
cggcttgttg cccgcttcga aaccaatgcc taaagagagg ttaaagccga cagcagcagt     1620
ttcatcaatc accacgatgc catgttcatc tgcccagtcg agcatctctt cagcgtaagg     1680
gtaatgcgag gtacggtagg agttggcccc aatccagtcc attaatgcgt ggtcgtgcac     1740
catcagcacg ttatcgaatc ctttgccacg caagtccgca tcttcatgac gaccaaagcc     1800
agtaaagtag aacggttttgt ggttaatcag gaactgttcg cccttcactg ccactgaccg     1860
gatgccgacg cgaagcgggt agatatcaca ctctgtctgg cttttggctg tgacgcacag     1920
ttcatagaga taaccttcac ccggttgcca gaggtgcgga ttcaccactt gcaaagtccc     1980
gctagtgcct tgtccagttg caaccacctg ttgatccgca tcacgcagtt caacgctgac     2040
atcaccattg ccaccaccct gccagtcaac agacgcgtgg ttacagtctt gcgcgacatg     2100
cgtcaccacg gtgatatcgt ccacccaggt gttcggcgtg gtgtagagca ttacgctgcg     2160
atggattccg gcatagttaa agaaatcatg gaagtaagac tgcttttttct tgccgttttc     2220 gtcggtaatc accattcccg gcgggatagt ctgccagttc agttcgttgt tcacacaaac     2280
ggtgatacgt acactttttcc cggcaataac atacggcgtg acatcggctt caaatggcgt     2340
atagccgccc tgatgctcca tcacttcctg attattgacc cacactttgc cgtaatgagt     2400
gaccgcatcg aaacgcagca cgatacgctg gcctgcccaa cctttcggta taaagacttc     2460
gcgctgatac cagacgttgc ccgcataatt acgaatatct gcatcggcga actgatcgtt     2520
aaaactgcct ggcacagcaa ttgcccggct ttcttgtaac gcgctttccc accaacgctg     2580
atcaattcca cagttttcgc gatccagact gaatgccac aggccgtcga gttttttgat      2640 ttcacggggtt gggggtttcta caggacggac catgagaaa aagtttcgat ctttggactc      2700
gctcacctaa acccactctc tgtcttcctc agatttaata aactttagag ggggtttggt     2760
```

```
gacgaagaag gtagccatca aaatccttca ccaacccacc tcaaacgatg gtgtatgagc    2820
atttcctatt agccaatgag aacctgccac gtgttacaga cagcaagtgg gaaggaaggt    2880
tttggttagg tgaagacttg aaagggttaa gatttggtgg ttttaaaatg ggcctccaag    2940
aagttactgg gccttttaa cacaaaaacc catgaaccaa tctaactcat aaataatcga    3000
ttgcggttta ctactagaat attggagagg aaacataaat cgaagagtaa ccggccagat    3060
tacctttaat cgaagacgat ggtaacatcc atgtctggat ccgatccaaa aaatcgggtt    3120
ctaggtcgga tctagatatg gtgaaatatc cgattgggta tgctttcatt tatgtttcgg    3180
gtaccggttc ggatcggata ttatccaaga ttcaaacata tccgaaaata cccgacagga    3240
atgtataagc ttatcggaaa ataatctcaa tctggtttag agtttggaac ataatcaaac    3300
cgggggatgt ctttttccag ttatatatgt cacaaacccc aaacaatcaa accgatctga    3360
ggttcggttt aggataaaacc acggcaattc ggaactctct ctcaatttgg tttagaatcc    3420
gagcaagtat tgagcttaac catttctttt tcgttcactt cctacgaaag catattcctt    3480
tctctctgta tctccttcac ctccgggcta aaaaggatc cggcttagag ctgcttgatg    3540
tttcgttttc ttctacttac gtggcgtgaa agctgatcaa aaacattatt cgacgcgaag    3600
cttcttcctg tctgaatagt gctgtataca cagacacaaa gctaaatcat tccaggtgat    3660
ctcttttgtc ttccatctga aactctagat tcagatcacc actatactcg agcctcattc    3720
gaaaaagctg tgaactttat aggggaacta acactgtaga cactagaaag atctttacgg    3780
gtttgatgat gatgatgatt cacttcaaga tctagaatat tagttgggtt tttgtctgaa    3840
aaggaacatt ctttgtagga gggttttgtc tgaaacagag agattcagtt ttcaagtcca    3900
tggagtccga tgagagtggt ctcccagcta tggagattga atgcagaatc actggcactt    3960
tgaacggtgt tgagtttgaa ctggtgggag gtggcgaagg gacacctgaa caagggagga    4020
tgacaaacaa gatgaagtcc accaaaggtg cattgacctt ctctccgtat cttctcagcc    4080
atgtcatggg ttacggtttc tatcactttg gcacctatcc gagtggctat gagaatccct    4140
ttcttcatgc catcaacaat ggaggttaca ccaacacacg aattgagaag tatgaagatg    4200
gtggagtgct ccacgtctcc ttctcttacc gttacgagtc tgggagggtc ataggagact    4260
tcaaagtgat gggaactggc tttccagaag attcagtcat cttcacagac aagatcatta    4320
gatccaatgc aactgttgag catcttcacc caatgggaga caatgacctg gatgggtcat    4380
tcacaagaac cttctctctg cgtgatggag gctactatag ctctgttgtg gactcacaca    4440
tgcacttcaa aagtgccatt catcctagca tcttgcagaa tggtggaccc atgtttgcct    4500
ttcgaagggt ggaagaggat cactcaaaca ccgaacttgg catagttgag taccagcatg    4560
ccttcaagac tcctgatgca gatgctgggg aagagtgagt agttagctta atcacctaga    4620
gctcgaattt ccccgatcgt tcaaacattt ggcaataaag tttcttaaga ttgaatcctg    4680
ttgccggtct tgcgatgatt atcatataat ttctgttgaa ttcgttaag catgtaataa    4740 ttaacatgta atgcatgacg ttatttatga gatgggtttt tatgattaga gtcccgcaat    4800
tatacattta atacgcgata gaaaacaaaa tatagcgcgc aaactaggat aaattatcgc    4860
gcgcggtgtc atctatgtta ctagatcg                                       4888
```

<210> SEQ ID NO 21
<211> LENGTH: 4888
<212> TYPE: DNA
<213> ORGANISM: Artificial Sequence
<220> FEATURE:

<223> OTHER INFORMATION: Expression cassette from pDAB100333

<400> SEQUENCE: 21

```
gagcataatt tttattaatg tactaaatta ctgttttgtt aaatgcaatt ttgctttctc      60
gggattttaa tatcaaaatc tatttagaaa tacacaatat tttgttgcag gcttgctgga     120
gaatcgatct gctatcataa aaattacaaa aaaattttat ttgcctcaat tattttagga     180
ttggtattaa ggacgcttaa attatttgtc gggtcactac gcatcattgt gattgagaag     240
atcagcgata cgaaatattc gtagtactat cgcgataatt tatttgaaaa ttcatatgaa     300
aagcaaacgt tacatgaatt gatgaaacaa tacaaagaca gataaagcca cgcacattta     360
ggatattggc cgagattact gaatattgag taagatcacg gaatttctga caggagcatg     420
tcttcaattc agcccaaatg gcagttgaaa tactcaaacc gccccatatg caggagcgga     480
tcattcattg tttgtttggt tgcctttgcc aacatgggag tccaaggttt ggtgacctcg     540
aggcttaaga ctttactaaa acttcaaaag aaaaacaata taaaaacgat aatccaaatg     600
cattattgat ctatataaca tcaagacaaa atacatatg tgactcttat tcaggtctta      660
ggtttattac agcaaagatc atgacttgat cacttcaaac aaagtacgta actataaaaa     720
cgagtcaaat agattgtctt acactaacgt gtcgataaa taatttgacc aaaaggtgat      780
cttattacag aaatagccac tgagctcggt agcaattccc gaggctgtag ccgacgatgg     840
tgcgccagga gagttgttga ttcattgttt gcctccctgc tgcggttttt caccgaagtt     900
catgccagtc cagcgttttt gcagcagaaa agccgccgac ttcggtttgc ggtcgcgagt     960
gaagatccct ttcttgttac cgccaacgcg caatatgcct tgcgaggtcg caaaatcggc    1020
gaaattccat acctgttcac cgacgacggc gctgacgcga tcaaagacgc ggtgatacat    1080
atccagccat gcacactgat actcttcact ccacatgtcg gtgtacattg agtgcagccc    1140
ggctaacgta tccacgccgt attcggtgat gataatcggc tgatgcagtt tctcctgcca    1200
ggccagaagt tcttttttcca gtaccttctc tgccgtttcc aaatcgccgc tttggacata    1260
ccatccgtaa taacggttca ggcacagcac atcaaagaga tcgctgatgg tatcggtgtg    1320
agcgtcgcag aacattacat tgacgcaggt gatcggacgc gtcgggtcga gtttacgcgt    1380
tgcttccgcc agtggcgcga aatattcccg tgcaccttgc ggacgggtat ccggttcgtt    1440
ggcaatactc cacatcacca cgcttgggtg gttttttgtca cgcgctatca gctctttaat    1500
cgcctgtaag tgcgcttgct gagtttcccc gttgactgcc tcttcgctgt acagttcttt    1560
cggcttgttg cccgcttcga aaccaatgcc taaagagagg ttaaagccga cagcagcagt    1620
ttcatcaatc accacgatgc catgttcatc tgcccagtcg agcatctctt cagcgtaagg    1680
gtaatgcgag gtacggtagg agttggcccc aatccagtcc attaatgcgt ggtcgtgcac    1740
catcagcacg ttatcgaatc ctttgccacg caagtccgca tcttcatgac gaccaaagcc    1800
agtaaagtag aacggtttgt ggttaatcag gaactgttcg cccttcactg ccactgaccg    1860
gatgccgacg cgaagcgggt agatatcaca ctctgtctgg cttttggctg tgacgcacag    1920
ttcatagaga taaccttcac ccggttgcca gaggtgcgga ttcaccactt gcaaagtccc    1980
gctagtgcct tgtccagttg caaccacctg ttgatccgca tcacgcagtt caacgctgac    2040
atcaccattg gccaccacct gccagtcaac agacgcgtgg ttacagtctt gcgcgacatg    2100
cgtcaccacg tgatatcgt ccacccaggt gttcggcgtg gtgtagagca ttacgctgcg     2160
atggattccg gcatagttaa agaaatcatg gaagtaagac tgcttttttct tgccgttttc    2220
gtcggtaatc accattcccg gcgggatagt ctgccagttc agttcgttgt tcacacaaac    2280
```

```
ggtgatacgt acactttcc cggcaataac atacggcgtg acatcggctt caaatggcgt    2340
atagccgccc tgatgctcca tcacttcctg attattgacc cacactttgc cgtaatgagt    2400
gaccgcatcg aaacgcagca cgatacgctg gcctgcccaa cctttcggta taaagacttc    2460
gcgctgatac cagacgttgc ccgcataatt acgaatatct gcatcggcga actgatcgtt    2520
aaaactgcct ggcacagcaa ttgcccggct ttcttgtaac gcgctttccc accaacgctg    2580
atcaattcca cagttttcgc gatccagact gaatgcccac aggccgtcga gttttttgat    2640
ttcacgggtt ggggtttcta caggacggac catggacttg aaaactgaat ctctctgttt    2700
cagacaaaac cctcctacaa agaatgttcc ttttcagaca aaaacccaac taatattcta    2760
gatcttgaag tgaatcatca tcatcatcaa acccgtaaag atctttctag tgtctacagt    2820
gttagttccc ctataaagtt cacagctttt tcgaatgagg ctcgagtata gtggtgatct    2880
gaatctagag tttcagatgg aagacaaaag agatcacctg gaatgattta gctttgtgtc    2940
tgtgtataca gcactattca gacaggaaga agcttcgcgt cgaataatgt ttttgatcag    3000 cttcacgcc acgtaagtag aagaaaacga acatcaagc agctctaagc cggatccttt    3060
tttagcccgg aggtgaagga gatacagaga gaaggaata tgcttcgta ggaagtgaac    3120 gaaaagaaa tggttaagct caatacttgc tcggattcta aaccaaattg agagagagtt    3180
ccgaattgcc gtggtttatc ctaaaccgaa cctcagatcg gtttgattgt ttggggtttg    3240
tgacatatat aactggaaaa agacatcccc cggtttgatt atgttccaaa ctctaaacca    3300
gattgagatt attttccgat aagcttatac attcctgtcg ggtattttcg gatatgtttg    3360
aatcttggat aatatccgat ccgaaccggt acccgaaaca taaatgaaag catacccaat    3420
cggatatttc accatatcta gatccgacct agaacccgat ttttggatc ggatccagac    3480 atggatgtta ccatcgtctt cgattaaagg taatctggcc ggttactctt cgatttatgt    3540
ttcctctcca atattctagt agtaaaccgc aatcgattat ttatgagtta gattggttca    3600 tgggttttttg tgttaaaaag gcccagtaac ttcttggagg cccatttta aaccaccaaa    3660 tcttaccct ttcaagtctt cacctaacca aaaccttcct tcccacttgc tgtctgtaac    3720
acgtggcagg ttctcattgg ctaataggaa atgctcatac accatcgttt gaggtgggtt    3780
ggtgaaggat tttgatggct accttcttcg tcaccaaacc ccctctaaag tttattaaat    3840
ctgaggaaga cagagagtgg gtttaggtga gcgagtccaa agatcgaaac ttttctcca    3900 tggagtccga tgagagtggt ctcccagcta tggagattga atgcagaatc actggcactt    3960
tgaacggtgt tgagtttgaa ctggtgggag gtggcgaagg gacacctgaa caagggagga    4020
tgacaaacaa gatgaagtcc accaaaggtg cattgacctt ctctccgtat cttctcagcc    4080
atgtcatggg ttacggtttc tatcactttg gcacctatcc gagtggctat gagaatccct    4140
ttcttcatgc catcaacaat ggaggttaca ccaacacacg aattgagaag tatgaagatg    4200
gtggagtgct ccacgtctcc ttctcttacc gttacgaggc tggagggtc ataggagact    4260 tcaaagtgat gggaactggc tttccagaag attcagtcat cttcacagac aagatcatta    4320
gatccaatgc aactgttgag catcttcacc caatgggaga caatgacctg gatgggtcat    4380
tcacaagaac cttctctctg cgtgatggag gctactatag ctctgttgtg gactcacaca    4440
tgcacttcaa aagtgccatt catcctagca tcttgcagaa tggtggaccc atgtttgcct    4500
ttcgaagggg ggaagaggat cactcaaaca ccgaacttgg catagttgag taccagcatg    4560
ccttcaagac tcctgatgca gatgctgggg aagagtgagt agttagctta atcacctaga    4620
```

```
gctcgaattt ccccgatcgt tcaaacattt ggcaataaag tttcttaaga ttgaatcctg    4680
ttgccggtct tgcgatgatt atcatataat ttctgttgaa ttcgttaag catgtaataa     4740 ttaacatgta atgcatgacg ttatttatga gatgggtttt tatgattaga gtcccgcaat    4800
tatacattta atacgcgata gaaaacaaaa tatagcgcgc aaactaggat aaattatcgc    4860
gcgcggtgtc atctatgtta ctagatcg                                       4888
```

<210> SEQ ID NO 22
<211> LENGTH: 739
<212> TYPE: DNA
<213> ORGANISM: Artificial Sequence
<220> FEATURE:
<223> OTHER INFORMATION: alternative BBCP sequence 739 nt

<400> SEQUENCE: 22

```
acagagagaa agtaatatgc tttagtgcga agtgaacgaa aaagaaatgg ttaagctcaa      60
tacttactcg gattctaaac caaattgaga gataattccg acttgccgtg gtttatcgta    120
aaccgaacct cagatcggta taattgtttg gtgtgtgtga catatataac tggaaaaaga    180
catcccgcgg tttcattatg ttccaaactc taaacgagat tgagattatt ttcggataag    240
cttatacatt cctgccgggt attttcgtat atgtctgatt cgtggataat atccgatccg    300
aaccggtacc cgaatcataa ctgaaagcat acccaatccg atagttcacc agctctagat    360
cggaccgaga acccgatttt ttggatagga tccagacttg gaggtcacca tcgtcttcga    420
ttaaaggaaa tctggtcggt tactcctcga tttctgtttc ctctccaata ttccagtagt    480
aaaccgcgat caattattta tgagttggat tggttcatgg gttttgtcg taaaaaggcc     540 cactatcttc ttggaggccc attttaaaac caccaaatct taacccttc aagtcttcac     600 ctaaccaaaa ccttcctacc cacttgctgt ctgtagcacg cggcaggttc tcattggcta    660
ataggaaatg ctcatacacc atcgtttgag gtgggttggt taaggatttt gatggctacc    720
ttcttcgtca ccaacccc                                                  739
```

<210> SEQ ID NO 23
<211> LENGTH: 739
<212> TYPE: DNA
<213> ORGANISM: Artificial Sequence
<220> FEATURE:
<223> OTHER INFORMATION: additional alternative BBCP sequence 739 nt

<400> SEQUENCE: 23

```
acagagagaa aggaatatgc tttcgtagga agtgaacgaa aaagacatgg ttaagctcaa     60
tacatgctgg gattctaaac caaattgaga gagagttccg aattgccgtg gtttatccta    120
aaccggacct cgaatcggtt tgattgtttg ggatttgtga caaatctaac tggaaaaaga    180 catccccgg tttgattatg ttccaaactc tgaaccagat tgagagtatt ttccgataag    240
cttatacatt cctgtcgggt attttgggat attttttgaat cttggataat atccgatccg    300
aaccggtccc cgagacttaa atgaaagcat accaactcgg attttgcacc atatctagat    360
ccgtcctaga acacgatttt ttggatcgga tccagacaag gatgtaacca tcttcttcga    420
ttaaaggtaa tctgaccggt tactctccga tttcgtttc ctctcgaata ttctcgtagt     480
aaaccgcaat cgattattga tgagttagat tggttcatgg gtctttgtgt taaaaaggcc    540
cagtaacttc ttggaggccc aatttaaaac cacaaaatct taaccatttc aagtcttaac    600
caaagcataa ccttccttcc cacttgctgt ttgtaacacg tgtcaggtgc tcatggagta    660
ataggaaatg ctcatacacc atcgtttgag gagggttggt gaacgatttt gatggctacc    720
```

```
ttcttcgtca ccaaacccc                                               739
```

<210> SEQ ID NO 24
<211> LENGTH: 739
<212> TYPE: DNA
<213> ORGANISM: Artificial Sequence
<220> FEATURE:
<223> OTHER INFORMATION: Additional alternative BBCP sequence 739 nt

<400> SEQUENCE: 24

```
acagagagaa aggaatatgc tttcgtagga agcgagcgaa aaagaaatgg ttaagctcta    60
tagttgctcg gattctaaac caaattgaga gagtgttccg tattgccgtg gtttattcta   120
aaccgaacct cagatcggtt tgattgtttg gggtttgtca catatctaac tggaaaaaga   180
catgccccgg tttgattagg ttctaaactc ttaacgagat tgagattatt gtccgataag   240
cttatacatt cctttcgagt attttcggat ttatttgaat cttggataat atccgatccg   300
aaccggaacc cggaaaataa atgaaagcat acccaatcgg atacttcacc atatctagat   360
cccccctaga acccgatttt ctggctcgga tccagacatg gatgtaatca tcgtcttcga   420
ttaaatgtaa tctggctggt tactcttcga tttatgttcc ctttccaata ttctaatcgt   480
aaaccgcaat cgattatcta tgagttagat tgcttcatgg gtttttgtgt taaataggcc   540
cagtaactgc ttggaggccc attttaaaac caccaaatct taacccttc acttcttcac    600
ctaaccaaaa ccttccttcc aacttgctgt ctgtaacacg tggcaggttc tcagtggcaa   660
atgggaaatg atcatacacc agcgtttgag gtgggttggt gaaggatttt gatggctacc   720
tgcttcgtca ccataccccc                                               739
```

<210> SEQ ID NO 25
<211> LENGTH: 739
<212> TYPE: DNA
<213> ORGANISM: Artificial Sequence
<220> FEATURE:
<223> OTHER INFORMATION: alternative BBCP sequence 739 nt

<400> SEQUENCE: 25

```
acagagaaaa aggaatatgc tttcgcagga agtgaacgaa aaagaaaggg ttaagctcac    60
tacttgctcg ttttctaaac caaattgaga gagagttccg aattgccgtg gtttctccga   120
aaccgaagct cagatcggtt tgcttgtttg gggtttgtga catatatatc tggaaaaaga   180
gatcccccgg ttggattatg ttccaaactc taaaccagat tgagattatt ttccgataag   240
ctcatacatt cctgtcgtgt atgttcggat atgtttgaat cttggataat atccgatccg   300
aaccggttcc cgaaacataa ataaaagcat acccaatcgg atatttcacc atgtcgagat   360
caggcctaga acccgatgtt atggatcgaa tccagacatg gattttgcca tcgtcttcga   420
ttcaatgtaa tctggccggt tactcttcga tttatgtttc ctctccaatc tactagtagc   480
aaaccgcgat cgatggttta tgagttagat tggttcgtgg gttattgtgt taaacaggcc   540
cagtaacttc ttggaggccc attgtaaaac caccaaatct taacccattc aagtcttccc   600
ctaaccaaaa ccttccgtcc cacttgctga cggtaacacg tggcaggttt tcattggcta   660
atagtagatg ctcatacacc atcgtttgag gtgggttggt gaaggattct gatgcctacc   720
ttcttcgtca ccaaaccccc                                               739
```

<210> SEQ ID NO 26
<211> LENGTH: 179
<212> TYPE: DNA

<213> ORGANISM: Brassica napus

<400> SEQUENCE: 26

```
aaaaacccctt ttttttttacc actgcactaa aaagaccttaa aagcccatttt gtcttttcttt    60 tttgatccaa ttgagatcag tttcctctgt tgtcactgta agattacgaa aaacaaagag       120
tattaagatt gcttgcttgt accttaaact gtttgatgca atcgttgaat cagttttgg        179
```

<210> SEQ ID NO 27
<211> LENGTH: 90
<212> TYPE: DNA
<213> ORGANISM: Brassica napus

<400> SEQUENCE: 27

```
aggtttgctt ctttctttgt ttgcttagtg ttgcgttttt aacggcgtga ggatgaagaa        60
aggttctgac tttgttgtgg ttttataggg                                        90
```

<210> SEQ ID NO 28
<211> LENGTH: 94
<212> TYPE: DNA
<213> ORGANISM: Brassica napus

<400> SEQUENCE: 28

```
aggtaaggtt aaggacttat tctgttagtt agttttgatt attttaagaa tcggtcttgt        60
actgatgctt tttagttggg tttgtttacc agtt                                   94
```

<210> SEQ ID NO 29
<211> LENGTH: 141
<212> TYPE: DNA
<213> ORGANISM: Brassica napus

<400> SEQUENCE: 29

```
gagtttgtaa tttcagcatt tgctatgtga aaagttgcag caatctttgt tcatcacact        60
gcgttagctt gacatgattt tagcttttgt atggtttctt gattgacaca ttagacatgt       120
ttttgcattt ttcaggtgaa g                                                141
```

<210> SEQ ID NO 30
<211> LENGTH: 85
<212> TYPE: DNA
<213> ORGANISM: Brassica napus

<400> SEQUENCE: 30

```
aagtaagagt tgtttctaaa atcactgaac ttataattag attgacagaa gagtgactaa        60
ccaaatggta aaatttgatt caggt                                             85
```

<210> SEQ ID NO 31
<211> LENGTH: 137
<212> TYPE: DNA
<213> ORGANISM: Brassica napus

<400> SEQUENCE: 31

```
aggtaacact aagtttataa taaaatttgc ttagttcaat tttttttttgt ctttctaagg       60 cttggctagt tgtgtcactt gtgtgtaaca tatgaagaat ctaagtttag ttttttttgg      120
tgatgaatct caaaggg                                                     137
```

<210> SEQ ID NO 32
<211> LENGTH: 87
<212> TYPE: DNA
<213> ORGANISM: Brassica napus

```
<400> SEQUENCE: 32
tggtaagcac accctctaat tgtttttttt aaagattcat agtcacttag ttctcctctc      60
atccattctt ttttatcata tatagtg                                         87

<210> SEQ ID NO 33
<211> LENGTH: 98
<212> TYPE: DNA
<213> ORGANISM: Brassica napus

<400> SEQUENCE: 33
aggtaaaaca tttttctttc tgtctcgctc tcactctcac tctcttggtt ttatgtgctc      60
agtctaagtt aagttctgca taacttttgc gtacagct                             98
```

CONSTRUCT AND METHOD FOR EXPRESSING TRANSGENES USING A *BRASSICA* BIDIRECTIONAL CONSTITUTIVE PROMOTER

CROSS-REFERENCE TO RELATED APPLICATIONS

This application claims priority under 35 U.S.C. §119 of U.S. provisional patent application Ser. No. 61/656,634 filed Jun. 7, 2012, which application is hereby incorporated by reference in its entirety. This application is also a continuation-in-part of Ser. No. 12/284,888 filed Sep. 25, 2008, which claims priority of U.S. provisional patent application Ser. No. 60/995,557, filed Sep. 27, 2007, the disclosure of both are incorporate by reference in their entireties.

FIELD OF THE INVENTION

This invention is generally related to the field of plant molecular biology, and more specifically the field of stable expression of multiple genes in transgenic plants.

BACKGROUND OF THE INVENTION

Many plant species are capable of being transformed with transgenes from other species to introduce agronomically desirable traits or characteristics, for example, improving nutritional value quality, increasing yield, conferring pest or disease resistance, increasing drought and stress tolerance, improving horticultural qualities (such as pigmentation and growth), imparting herbicide resistance, enabling the production of industrially useful compounds and/or materials from the plant, and/or enabling the production of pharmaceuticals. The introduction of transgenes into plant cells and the subsequent recovery of fertile transgenic plants that contain a stably integrated copy of the transgene can be used to produce transgenic plants that possess the desirable traits.

Control and regulation of gene expression can occur through numerous mechanisms. Transcription initiation of a gene is a predominant controlling mechanism of gene expression. Initiation of transcription is generally controlled by polynucleotide sequences located in the 5'-flanking or upstream region of the transcribed gene. These sequences are collectively referred to as promoters and are categorized as a gene regulatory element. Promoters in plants that have been cloned and widely used for both basic research and biotechnological application are generally unidirectional, directing only one gene that has been fused at its 3' end (i.e., downstream). See, for example, Xie et al. (2001) Nat. Biotechnol. 19(7):677-9; U.S. Pat. No. 6,388,170.

Additional gene regulatory elements include sequences that interact with specific DNA-binding factors. These sequence motifs are sometimes referred to as cis-elements, and are usually position- and orientation-dependent, though they may be found 5' or 3' to a gene's coding sequence, or in an intron. Such cis-elements, to which tissue-specific or development-specific transcription factors bind, individually or in combination, may determine the spatiotemporal expression pattern of a promoter at the transcriptional level. These cis-elements vary widely in the type of control they exert on operably linked genes. Some elements act to increase the transcription of operably-linked genes in response to environmental responses (e.g., temperature, moisture, and wounding). Other cis-elements may respond to developmental cues (e.g., germination, seed maturation, and flowering) or to spatial information (e.g., tissue specificity). See, for example, Langridge et al. (1989) Proc. Natl. Acad. Sci. USA 86:3219-23.

It is often necessary to introduce multiple genes into plants for metabolic engineering and trait stacking, which genes are frequently controlled by identical or homologous promoters. However, homology-based gene silencing (HBGS) is likely to arise when multiple introduced transgenes have homologous promoters driving them. See e.g., Mol et al. (1989) Plant Mol. Biol. 13:287-94. HBGS has been reported to occur extensively in transgenic plants. See e.g., Vaucheret and Fagard (2001) Trends Genet. 17:29-35. Several mechanisms have been suggested to explain the phenomena of HBGS, all of which include the feature that sequence homology in the promoter triggers cellular recognition mechanisms that result in silencing of the repeated genes. See e.g., Matzke and Matzke (1995) Plant Physiol. 107:679-85; Meyer and Saedler (1996) Ann. Rev. Plant Physiol. Plant Mol. Biol. 47:23-48; Fire (1999) Trends Genet. 15:358-63; Hamilton and Baulcombe (1999) Science 286:950-2; and Steimer et al. (2000) Plant Cell 12:1165-78.

Strategies to avoid HBGS in transgenic plants frequently involve the development of various promoters that are functionally equivalent but have minimal sequence homology. Thus, there remains a need for constructs and methods for stable expression of multiple transgenes effectively with minimum risk for recombination or loss of transgenes through breeding or multiple generations in transgenic plants.

SUMMARY OF THE INVENTION

Provided are constructs and methods for expressing multiple genes in plant cells and/or plant tissues using a disclosed bidirectional promoter from *Brassica napus* or *Brassica* bidirectional constitutive promoter (BBCP). The constructs provided comprise at least one such bi-directional promoter linked to multiple gene expression cassettes, wherein each of the gene expression cassettes comprises at least one transgene. In some embodiments, the constructs and methods provided allow expression of genes between two and twenty.

In one aspect, provided is a nucleic acid construct for expressing multiple genes in plant cells and/or tissues. The nucleic acid construct comprises (a) a bi-directional promoter comprising a nucleotide sequence having at least 80% identity to SEQ ID NO: 1; and (b) two gene expression cassettes on opposite ends of the bi-directional promoter.

In one embodiment, the bi-directional promoter comprises at least one enhancer. In another embodiment, the bi-directional promoter does not comprise an enhancer. In another embodiment, the nucleic acid construct comprises a binary vector for plant transformation. In another embodiment, the nucleic acid construct comprises a binary vector for *Agrobacterium*-mediated transformation. In another embodiment, the bi-directional promoter comprises at least one intron. In another embodiment, the bi-directional promoter comprises at least one 5' untranslated region. In one embodiment, the bi-directional promoter comprises a nucleotide sequence selected from SEQ ID NO: 2 or 3. In another embodiment, the bi-directional promoter comprising a nucleotide sequence having at least 85%, 90%, 95%, or 100% identity to SEQ ID NO: 1. In another embodiment, the bi-directional promoter comprises a nucleotide sequence selected from SEQ ID NOs: 1, 22-25, or their complements. In a further or alternative embodiment, the bi-directional promoter comprises a nucleotide sequence selected from SEQ ID NOs: 1, 22-24, or their complements. In a further or alternative embodiment, the bi-directional promoter comprises a nucleotide sequence selected from SEQ ID NOs: 1, 22-23, or their complements. In a further or alternative embodiment, the bi-directional promoter comprises a nucleotide sequence selected from SEQ ID NO: 1, 22, or their complements.

In one embodiment, at least one of the gene expression cassettes comprises two or more genes linked via a translation switch. In another embodiment, both the gene expression cassettes comprise two or more genes linked via a translation switch. In a further or alternative embodiment, the translation switch is selected from the group consisting of an internal ribosome entry site (IRES), an alternative splicing site, a ribozyme cleavage site, a polynucleotide sequence coding a 2A peptide, a polynucleotide sequence coding a 2A-like peptide, a polynucleotide sequence coding an intein, a polynucleotide sequence coding a protease cleavage site, and combinations thereof. In a further or alternative embodiment, the translation switch comprises a cis-acting hydrolase element (CHYSEL). In a further embodiment, the CHYSEL is a 2A or 2A-like peptide sequence. In another embodiment, a gene upstream of the translational switch does not comprise a translation stop codon.

In one embodiment, the nucleic acid construct comprises at least one transgene. In another embodiment, the nucleic acid construct enables or allows expression of at least four genes. In a further embodiment, all four genes are transgenes. In another embodiment, the nucleic acid construct enables expression of genes between three and twenty. In another embodiment, the nucleic acid construct enables expression of genes between four and eight. In a further or alternative embodiment, the genes are transgenes. In another embodiment, at least one gene expression cassette comprises a polynucleotide sequence encoding a fusion protein. In a further embodiment, the fusion protein comprises three to five genes. In another embodiment, both the gene expression cassettes do not comprises a EPSPS gene or paralog.

In another aspect, provided is a nucleic acid construct comprising a regulatory element useful for terminating the expression of a single or multiple genes in plant cells and/or tissues. The regulatory element comprises a paralog A 3' untranslated region (UTR) or poly A region which can be fused to the 3' end of a transgene. In one embodiment, the paralog A 3' UTR comprises a functional polyadenylation sequence that is useful for the termination and regulation of transcription and translation. In a further or alternative embodiment, the regulatory element comprises a polynucleotide sequence having at least 80%, 85%, 90%, 95% or 100% identity to SEQ ID NO: 26 or its complement. In a further embodiment, the regulatory element comprises a polynucleotide sequence of SEQ ID NO: 26 or its complement.

In another aspect, provided is a method for generating a transgenic plant, comprising transforming a plant cell with the nucleic acid construct provided herein. In another aspect, provided is a method for generating a transgenic cell, comprising transforming the cell with the nucleic acid construct provided herein. In another aspect, provided is a plant cell comprising the nucleic acid construct provided herein. In a further or alternative embodiment, the nucleic acid construct is stably transformed into the plant cell. In another aspect, provided is a transgenic plant or seed comprising the nucleic acid construct provided herein. In a further or alternative embodiment, the nucleic acid construct is stably transformed into cells of the transgenic plant or seed. In a further embodiment, the transgenic plant is a dicotyledonous plant. In another further embodiment, the transgenic plant is a monocotyledonous plant. In another aspect, provide is a method for expressing multiple genes in plant cells and/or tissues, comprising introducing into the plant cells and/or tissues the nucleic acid construct provided herein. In a further or alternative embodiment, the plant cells and/or tissues are stably transformed with the nucleic acid construct provided herein.

In another aspect, provided is a binary vector for *Agrobacterium*-mediated transformation. The binary vector comprises the nucleic acid construct provided herein. In another aspect, provided is the use of a bi-directional promoter provided herein for multiple-transgenes expression in plants. In one embodiment, the bi-directional promoter comprising a nucleotide sequence having at least 80%, 85%, 90%, 95% or 100% identity to SEQ ID NO: 1. In another aspect, provided is the use of a bi-directional promoter provided herein in the manufacturing of transgenic plants or seeds. In one embodiment, the bi-directional promoter comprising a nucleotide sequence having at least 80%, 85%, 90%, 95% or 100% identity to SEQ ID NO: 1.

In another aspect, provided is a nucleic acid construct comprising at least one *Brassica* intron sequence in transgenic plant cells and/or tissues. In one embodiment, the *Brassica* intron sequence is selected from SEQ ID NOs: 27-33. In another aspect, provided is the use of at least one *Brassica* intron sequence in the manufacturing of transgenic plants or seeds. In one embodiment, the *Brassica* intron sequence is selected from SEQ ID NOs: 27-33.

DETAILED DESCRIPTION OF THE INVENTION

Development of transgenic products is becoming increasingly complex, which requires stacking multiple transgenes into a single locus. Traditionally each transgene usually requires a unique promoter for expression, so multiple promoters are required to express different transgenes within one gene stack. In addition to increasing the size of the gene stack, this frequently leads to repeated use of the same promoter to obtain similar levels of expression patterns of different transgenes for expression of a single polygenic trait. Multi-gene constructs driven by the same promoter are known to cause gene silencing, thus making transgenic products less efficacious in the field. Excess of transcription factor (TF)-binding sites due to promoter repetition can cause depletion of endogenous TFs leading to transcriptional inactivation. The silencing of transgenes will likely undesirably affect the performance of a transgenic plant produced to express the transgenes. Repetitive sequences within a transgene may lead to gene intra-locus homologous recombination resulting in polynucleotide rearrangements.

Provided are methods and constructs using a *Brassica* bidirectional constitutive promoter (BBCP) to express transgenes in plant. Also provided are methods and constructs combining the bidirectional promoter system with bicistronic organization of genes on either one or both ends of the promoter, for example with the use of a 2A sequence from Thosea asigna virus. The 2A protein, which is only 16-20 amino acids long, cleaves the polyprotein at its own carboxyl-terminus. This "self-cleavage" or "ribosome skip" property of the 2A or 2A-like peptide can be used to process artificial polyproteins produced in transgenic plants. In one embodiment, Cry34 and Cry35 genes are fused in one gene expression cassette, where GFP (or YFP or PhiYFP) and AAD1 genes are fused into another gene expression cassette (with a single open reading frame (ORF) with a copy of the 2A protein gene placed between the two genes in each combination). For example, each of these gene expression cassettes (or gene pairs) can be placed on the either end of the bidirectional promoter to drive 4 transgenes using a single promoter. Thus, the constructs and methods provided herein are useful to avoid repeated use of the same promoter and significantly reduce the size of commercial constructs. In addition, driving four or more genes with one promoter also provides ability to co-express genes controlling a single polygenic trait.

Plant promoters used for basic research or biotechnological application are generally unidirectional, directing only one gene that has been fused at its 3' end (downstream). It is often necessary to introduce multiple genes into plants for metabolic engineering and trait stacking and therefore, multiple promoters are typically required in future transgenic crops to drive the expression of multiple genes. It is desirable to design strategies that can save the number of promoters deployed and allow simultaneous co-regulated expression for gene stacking. In some embodiment, the bi-directional promoters provided can drive transcription of multiple transcription units, including RNAi, artificial miRNA, or hairpin-loop RNA sequences.

Certain abbreviations disclosed are listed in Table 1.

TABLE 1

Abbreviations used in the disclosure

| Phrase | Abbreviation |
| --- | --- |
| bicinchoninic acid | BCA |
| cauliflower mosaic virus | CaMV |
| chloroplast transit peptide | CTP |
| homology-based gene silencing | HBGS |
| ZmUbi1 minimal core promoter | minUbi1P |
| oligo ligation amplification | OLA |
| phosphate buffered saline | PBS |
| phosphate buffered saline with 0.05% Tween 20 | PBST |
| polymerase chain reaction | PCR |
| rolling circle amplification | RCA |
| reverse transcriptase PCR | RT-PCR |
| single nucleotide primer extension | SNuPE |
| upstream regulatory sequence | URS |

As used herein, the articles, "a," "an," and "the" include plural references unless the context clearly and unambiguously dictates otherwise.

As used herein, the phrase "backcrossing" refers to a process in which a breeder crosses hybrid progeny back to one of the parents, for example, a first generation hybrid F1 with one of the parental genotypes of the F1 hybrid.

As used herein, the phrase "intron" refers to any nucleic acid sequence comprised in a gene (or expressed nucleotide sequence of interest) that is transcribed but not translated. Introns include untranslated nucleic acid sequence within an expressed sequence of DNA, as well as the corresponding sequence in RNA molecules transcribed therefrom.

The construct provided can also contain sequences that enhance translation and/or mRNA stability such as introns. An example of one such intron is the first intron of gene II of the histone H3.III variant of *Arabidopsis thaliana* or any other commonly known intron sequence. Chaubet et al. Journal of Molecular Biology, 225:569-574 (1992). It is known in the art that introns can be used in combination with a promoter sequences to enhance translation and/or mRNA stability.

As used herein, the phrase "5' untranslated region" or "5'UTR" refers to an untranslated segment in 5' terminus of the pre-mRNAs or mature mRNAs. For example, on mature mRNAs, the 5'UTR typically harbors on its 5' end a 7-methylguanosine cap and is involved in many processes such as splicing, polyadenylation, mRNA export towards the cytoplasm, identification of the 5' end of the mRNA by the translational machinery and protection of the mRNAs against degradation.

As used herein, the phrase "3' untranslated region" or "3'UTR" refers to an untranslated segment in 3' terminus of the pre-mRNAs or mature mRNAs. For example, on mature mRNAs this region harbors the poly (A) tail and is known to have many roles in mRNA stability, translation initiation, mRNA export.

As used herein, the phrase "polyadenylation signal" refers to a nucleic acid sequence present in the mRNA transcripts, that allows for the transcripts, when in the presence of the poly (A) polymerase, to be polyadenylated on the polyadenylation site, for example, located 10 to 30 bases downstream the poly (A) signal. Many polyadenylation signals are known in the art and are useful for the present invention. Examples include the human variant growth hormone polyadenylation signal, the SV40 late polyadenylation signal and the bovine growth hormone polyadenylation signal.

As used herein, the phrase "isolated" refers to biological component (including a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The phrase "isolated" also embraces nucleic acids and proteins prepared by recombinant expression in a host cell, as well as chemically-synthesized nucleic acid molecules, proteins, and peptides.

As used herein, the phrase "gene expression" refers to a process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, the phrase "homology-based gene silencing" (HBGS) refers to a generic term that includes both transcriptional gene silencing and posttranscriptional gene silencing. Silencing of a target locus by an unlinked silencing locus can result from transcription inhibition (transcriptional gene silencing; TGS) or mRNA degradation (post-transcriptional gene silencing; PTGS), owing to the production of double-stranded RNA (dsRNA) corresponding to promoter or transcribed sequences, respectively. The involvement of distinct cellular components in each process suggests that dsRNA-induced TGS and PTGS likely result from the diversification of an ancient common mechanism. However, a strict comparison of TGS and PTGS has been difficult to achieve because it generally relies on the analysis of distinct silencing loci. A single transgene locus can be described to trigger both TGS and PTGS, owing to the production of dsRNA corresponding to promoter and transcribed sequences of different target genes. See, for example, Mourrain et al. (2007) Planta 225:365-79. It is likely that siRNAs are the actual molecules that trigger TGS and PTGS on homologous sequences: the siRNAs would in this model trigger silencing and methylation of homologous sequences in cis and in trans through the spreading of methylation of transgene sequences into the endogenous promoter.

As used herein, the phrase "nucleic acid molecule" (or "nucleic acid" or "polynucleotide") refers to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The term may refer to a molecule of RNA or DNA of indeterminate length. The term includes single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by the sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" relative to a further element if they are bonded or would be bonded to the same nucleic acid in the 5' direction from that element. Similarly, discrete elements may be "downstream" relative to a further element if they are or would be bonded to the same nucleic acid in the 3' direction from that element.

As used herein, the phrase "base position," refers to the location of a given base or nucleotide residue within a designated nucleic acid. The designated nucleic acid may be defined by alignment (see below) with a reference nucleic acid.

As used herein, the phrase "hybridization" refers to a process where oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

As used herein, the phrases "specifically hybridizable" and "specifically complementary" refers to a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the chosen hybridization method and the composition and length of the hybridizing nucleic acid sequences. Generally, the temperature of hybridization and the ionic strength (especially the Na+ and/or Mg2+ concentration) of the hybridization buffer will contribute to the stringency of hybridization, though wash times also influence stringency. Calculations regarding hybridization conditions required for attaining particular degrees of stringency are discussed in Sambrook et al. (ed.), Molecular Cloning: A Laboratory Manual, 2nd ed., vol. 1-3, Cold Spring Harbor Laboratory Press, Cold Spring Harbor, N.Y., 1989, chs. 9 and 11.

As used herein, the phrase "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes.

The following are representative, non-limiting hybridization conditions:

Very High Stringency:
Hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency:
Hybridization in 5-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency:
Hybridization in 6×SSC buffer at room temperature to 55° C. for 16-20 hours; wash at least twice in 2×–3×SSC buffer at room temperature to 55° C. for 20-30 minutes each.

In particular embodiments, specifically hybridizable nucleic acid molecules can remain bound under very high stringency hybridization conditions. In these and further embodiments, specifically hybridizable nucleic acid molecules can remain bound under high stringency hybridization conditions. In these and further embodiments, specifically hybridizable nucleic acid molecules can remain bound under moderate stringency hybridization conditions.

As used herein, the phrase "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer," which allows a DNA polymerase to extend the oligonucleotide and replicate the complementary strand.

As used herein, the phrase "sequence identity" or "identity," refers to a context where two nucleic acid or polypeptide sequences, may refer to the residues in the two sequences that are the same when aligned for maximum correspondence over a specified comparison window.

As used herein, the phrase "percentage of sequence identity" refers to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein, the phrase "operably linked" refers to a context where the first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

As used herein, the phrase "promoter" refers to a region of DNA that generally is located upstream (towards the 5' region of a gene) that is needed for transcription. Promoters may permit the proper activation or repression of the gene which they control. A promoter may contain specific sequences that are recognized by transcription factors. These factors may bind to the promoter DNA sequences and result in the recruitment of RNA polymerase, an enzyme that synthesizes RNA from the coding region of the gene.

As used herein, the phrase "transforms" or "transduces" refers to a process where a virus or vector transfers nucleic acid molecules into a cell. A cell is "transformed" by a nucleic acid molecule "transduced" into the cell when the nucleic acid molecule becomes stably replicated by the cell, either by incorporation of the nucleic acid molecule into the cellular genome or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) Nature 319:791-3); lipofection (Felgner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; whiskers-mediated transformation; and microprojectile bombardment (Klein et al. (1987) Nature 327:70).

As used herein, the phrase "transgene" refers to an exogenous nucleic acid sequence. In one example, a transgene is a gene sequence (e.g., an herbicide-resistance gene), a gene encoding an industrially or pharmaceutically useful compound, or a gene encoding a desirable agricultural trait. In yet another example, the transgene is an antisense nucleic acid sequence, wherein expression of the antisense nucleic acid sequence inhibits expression of a target nucleic acid sequence. A transgene may contain regulatory sequences operably linked to the transgene (e.g., a promoter). In some embodiments, a nucleic acid sequence of interest is a transgene. However, in other embodiments, a nucleic acid sequence of interest is an endogenous nucleic acid sequence, wherein additional genomic copies of the endogenous nucleic acid sequence are desired, or a nucleic acid sequence that is in the antisense orientation with respect to the sequence of a target nucleic acid molecule in the host organism.

As used herein, the phrase "vector" refers to a nucleic acid molecule as introduced into a cell, thereby producing a transformed cell. A vector may include nucleic acid sequences that permit it to replicate in the host cell, such as an origin of replication. Examples include, but are not limited to, a plasmid, cosmid, bacteriophage, or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector. A vector may optionally include materials to aid in achieving entry of the nucleic acid molecule into the cell (e.g., a liposome).

As used herein, the phrase "plant" includes plants and plant parts including but not limited to plant cells and plant tissues such as leaves, stems, roots, flowers, pollen, and seeds. The class of plants that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicotyledons plants and monocotyledons plants. Examples of dicotyledons plants include tobacco, *Arabidopsis*, soybean, tomato, papaya, canola, sunflower, cotton, alfalfa, potato, grapevine, pigeon pea, pea, *Brassica*, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledons plants include corn, rice, wheat, sugarcane, barley, rye, sorghum, orchids, bamboo, banana, cattails, lilies, oat, onion, millet, and triticale.

As used herein, the phrase "plant material" refers to leaves, stems, roots, flowers or flower parts, fruits, pollen, egg cells, zygotes, seeds, cuttings, cell or tissue cultures, or any other part or product of a plant. In some embodiment, plant material includes cotyledon and leaf.

As used herein, the phrase "translation switch" refers to a mechanism at end of a gene allowing translation of an immediate downstream gene. The mechanism of translation switch can function at nucleic acid level (for example, viral or eukaryotic internal ribosome entry site (IRES), an alternative splicing site, or a ribozyme cleavage site) or at peptide/protein level (for example, a 2A peptide, a 2A-like peptide, an intein peptide, or a protease cleavage site).

These mechanisms of translation switch at nucleic acid level or at peptide/protein level are well known in the art. See e.g., li, Z., H. M. Schumacher, et al. (2010) J Biotechnol 145(1): 9-16; Chen, Y., K. Perumal, et al. (2000) Gene Expr 9(3): 133-143; Dinkova, T. D., H. Zepeda, et al. (2005) Plant J 41(5): 722-731; Dorokhov, Y. L., M. V. Skulachev, et al. (2002) Proc Natl Acad Sci USA 99(8): 5301-5306; Fernandez-Miragall, O. and C. Hernandez (2011) PLoS One 6(7): e22617; Groppelli, E., G. J. Belsham, et al. (2007) J Gen Virol 88(Pt 5): 1583-1588; Ha, S. H., Y. S. Liang, et al. (2010) Plant Biotechnol J 8(8): 928-938; Karetnikov, A. and K. Lehto (2007) J Gen Virol 88(Pt 1): 286-297; Karetnikov, A. and K. Lehto (2008) Virology 371(2): 292-308; Khan, M. A., H. Yumak, et al. (2009) J Biol Chem 284(51): 35461-35470; and Koh, D. C., S. M. Wong, et al. (2003) J Biol Chem 278(23): 20565-20573, the content of which are hereby incorproated by reference in their entireties. Multi-gene expression constructs containing modified inteins have been disclosed in U.S. Pat. Nos. 7,026,526 and 7,741,530, as well as U.S. Patent application 2008/0115243, the content of which are hereby incorporated by reference in their entireties.

As used herein, the phrase "selectable marker" or "selectable marker gene" refers to a gene that is optionally used in plant transformation to, for example, protect the plant cells from a selective agent or provide resistance/tolerance to a selective agent. Only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include gene for neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide resistance including Bar (resistance against BASTA® (glufosinate ammonium), or phosphinothricin (PPT)), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. The phrase "marker-positive" refers to plants that have been transformed to include the selectable marker gene.

Various selectable or detectable markers can be incorporated into the chosen expression vector to allow identification and selection of transformed plants, or transformants. Many methods are available to confirm the expression of selection markers in transformed plants, including for example DNA sequencing and PCR (polymerase chain reaction), Southern blotting, RNA blotting, immunological methods for detection of a protein expressed from the vector, e.g., precipitated protein that mediates phosphinothricin resistance, or other proteins such as reporter genes β-glucuronidase (GUS), luciferase, green fluorescent protein (GFP), DsRed, β-galactosidase, chloramphenicol acetyltransferase (CAT), alkaline phosphatase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for the selection of transformed cells or tissues. Selectable marker genes include genes encoding antibiotic resistance, such as those encoding neomycin phosphotransferase II (NEO) and hygromycin phosphotransferase (HPT) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for the mutant target enzymes, 5-enolpyruvylshikimate-3-phosphate synthase (EPSPS). Genes and mutants for EPSPS have been disclosed in U.S. Pat. Nos. 4,940,835, 5,188,642, 5,310,667, 5,633,435, 5,633,448, and 6,566,587, the contents of which are incorporated by reference in their entireties. Resistance to glufosinate ammonium, bromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides. Enzymes/genes for glufosinate resistance/tolerance have been disclosed in U.S. Pat. Nos. 5,273,894, 5,276,268, 5,550,318, and 5,561,236, the contents of which are incorporated by reference in their entireties. Enzymes/genes for 2,4-D resistance have been previously disclosed in U.S. Pat. Nos. 6,100,446 and 6,153,401, as well as patent applications US 2009/0093366 and WO 2007/053482, the contents of which are hereby incorporated by reference in their entireties. Enzymes/genes for nitrilase has been previously disclosed in U.S. Pat. Nos. 4,810,648, the content of which is incorporated by reference in its entirety.

Other herbicides can inhibit the growing point or meristem, including imidazolinone or sulfonylurea, and genes for resistance/tolerance of acetohydroxyacid synthase (AHAS) and acetolactate synthase (ALS) for these herbicides have been described. Genes and mutants for AHAS and mutants have been disclosed in U.S. Pat. Nos. 4,761,373, 5,304,732, 5,331,107, 5,853,973, and 5,928,937, the contents of which are incorporated by reference in their entireties. Genes and mutants for ALS have been disclosed in U.S. Pat. Nos. 5,013,659 and 5,141,870, the contents of which are incorporated by reference in their entireties.

Glyphosate resistance genes include mutant 5-enolpyruvylshikimate-3-phosphate synthase (EPSPs) genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include glufosinate (phosphinothricin acetyl transferase (PAT) genes from Streptomyces species, including Streptomyces hygroscopicus and Streptomyces viridichromogenes), and pyridinoxy or phenoxy proprionic acids and cyclohexones (ACCase inhibitor-encoding genes). Herbicide resistance/tolerance genes of acetyl coemzyme A carboxylase (ACCase) have been described in U.S. Pat. Nos. 5,162,602 and 5,498,544, the contents of which are incorporated by reference in their entireties.

A DNA molecule encoding a mutant aroA gene can be obtained under ATCC accession number 39256, and the nucleotide sequence of the mutant gene is disclosed in U.S. Pat. No. 4,769,061 to Comai, European patent application No. 0 333 033 to Kumada et al., and U.S. Pat. No. 4,975,374 to Goodman et al., disclosing nucleotide sequences of glutamine synthetase genes which confer resistance to herbicides such as L-phosphinothricin. The nucleotide sequence of a PAT gene is provided in European application No. 0 242 246 to Leemans et al. Also DeGreef et al., Bio/Technology 7:61 (1989), describes the production of transgenic plants that express chimeric bar genes coding for PAT activity. Exemplary of genes conferring resistance to phenoxy proprionic acids and cyclohexones, including sethoxydim and haloxyfop, are the Acc1-S1, Acc1-S2 and Acc1-S3 genes described by Marshall et al., Theon. Appl. Genet. 83:435 (1992). GAT genes capable of conferring glyphosate resistance are described in WO 2005012515 to Castle et al. Genes conferring resistance to 2,4-D, fop and pyridyloxy auxin herbicides are described in WO 2005107437 and U.S. patent application Ser. No. 11/587,893.

Other herbicides can inhibit photosynthesis, including triazine (psbA and 1s+ genes) or benzonitrile (nitrilase gene). Przibila et al., Plant Cell 3:169 (1991), describes the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

For purposes of the present invention, selectable marker genes include, but are not limited to genes encoding: neomycin phosphotransferase II (Fraley et al. (1986) CRC Critical Reviews in Plant Science, 4:1-25); cyanamide hydratase (Maier-Greiner et al. (1991) Proc. Natl. Acad. Sci. USA, 88:4250-4264); aspartate kinase; dihydrodipicolinate synthase (Perl et al. (1993) Bio/Technology, 11:715-718); tryptophan decarboxylase (Goddijn et al. (1993) Plant Mol. Bio., 22:907-912); dihydrodipicolinate synthase and desensitized aspartate kinase (Perl et al. (1993) Bio/Technology, 11:715-718); bar gene (Toki et al. (1992) Plant Physiol., 100:1503-1507 and Meagher et al. (1996) and Crop Sci., 36:1367); tryptophan decarboxylase (Goddijn et al. (1993) Plant Mol. Biol., 22:907-912); neomycin phosphotransferase (NEO) (Southern et al. (1982) J. Mol. Appl. Gen., 1:327; hygromycin phosphotransferase (HPT or HYG) (Shimizu et al. (1986) Mol. Cell. Biol., 6:1074); dihydrofolate reductase (DHFR) (Kwok et al. (1986) PNAS USA 4552); phosphinothricin acetyltransferase (DeBlock et al. (1987) EMBO J., 6:2513); 2,2-dichloropropionic acid dehalogenase (Buchanan-Wollatron et al. (1989) J. Cell. Biochem. 13D:330); acetohydroxyacid synthase (Anderson et al., U.S. Pat. No. 4,761,373; Haughn et al. (1988) Mol. Gen. Genet. 221:266); 5-enolpyruvyl-shikimate-phosphate synthase (aroA) (Comai et al. (1985) Nature 317:741); haloarylnitrilase (Stalker et al., published PCT application WO87/04181); acetyl-coenzyme A carboxylase (Parker et al. (1990) Plant Physiol. 92:1220); dihydropteroate synthase (sul I) (Guerineau et al. (1990) Plant Mol. Biol. 15:127); and 32 kD photosystem II polypeptide (psbA) (Hirschberg et al. (1983) Science, 222:1346).

Also included are genes encoding resistance to: chloramphenicol (Herrera-Estrella et al. (1983) EMBO J., 2:987-992); methotrexate (Herrera-Estrella et al. (1983) Nature, 303:209-213; Meijer et al. (1991) Plant Mol. Bio., 16:807-820 (1991); hygromycin (Waldron et al. (1985) Plant Mol. Biol., 5:103-108; Zhijian et al. (1995) Plant Science, 108:219-227 and Meijer et al. (1991) Plant Mol. Bio. 16:807-820); streptomycin (Jones et al. (1987) Mol. Gen. Genet., 210:86-91); spectinomycin (Bretagne-Sagnard et al. (1996) Transgenic Res., 5:131-137); bleomycin (Hille et al. (1986) Plant Mol. Biol., 7:171-176); sulfonamide (Guerineau et al. (1990) Plant Mol. Bio., 15:127-136); bromoxynil (Stalker et al. (1988) Science, 242:419-423); 2,4-D (Streber et al. (1989) Bio/Technology, 7:811-816); glyphosate (Shaw et al. (1986) Science, 233:478-481); and phosphinothricin (DeBlock et al. (1987) EMBO J., 6:2513-2518). All references recited in the disclosure are hereby incorporated by reference in their entireties unless stated otherwise.

The above list of selectable marker and reporter genes are not meant to be limiting. Any reporter or selectable marker gene are encompassed by the present invention. If necessary, such genes can be sequenced by methods known in the art.

The reporter and selectable marker genes are synthesized for optimal expression in the plant. That is, the coding sequence of the gene has been modified to enhance expression in plants. The synthetic marker gene is designed to be expressed in plants at a higher level resulting in higher transformation efficiency. Methods for synthetic optimization of genes are available in the art. In fact, several genes have been optimized to increase expression of the gene product in plants.

The marker gene sequence can be optimized for expression in a particular plant species or alternatively can be modified for optimal expression in plant families. The plant preferred codons may be determined from the codons of highest frequency in the proteins expressed in the largest amount in the particular plant species of interest. See, for example, EPA 0359472; EPA 0385962; WO 91/16432; Perlak et al. (1991) Proc. Natl. Acad. Sci. USA, 88:3324-3328; and Murray et al. (1989) Nucleic Acids Research, 17: 477-498; U.S. Pat. No. 5,380,831; and U.S. Pat. No. 5,436,391, herein incorporated by reference. In this manner, the nucleotide sequences can be optimized for expression in any plant. It is recognized that all or any part of the gene sequence may be optimized or synthetic. That is, fully optimized or partially optimized sequences may also be used.

Genes that Confer Resistance to an Herbicide:

A. Resistance/tolerance of acetohydroxyacid synthase (AHAS) and acetolactate synthase (ALS) against herbicides imidazolinone or sulfonylurea. Genes and mutants for AHAS and mutants have been disclosed in U.S. Pat. Nos. 4,761,373, 5,304,732, 5,331,107, 5,853,973, and 5,928,937. Genes and mutants for ALS have been disclosed in U.S. Pat. Nos. 5,013,659 and 5,141,870.

B. Resistance/tolerance genes of acetyl coemzyme A carboxylase (ACCase) against herbicides cyclohexanediones and/or aryloxyphenoxypropanoic acid (including Haloxyfop, Diclofop, Fenoxyprop, Fluazifop, Quizalofop) have been described in U.S. Pat. Nos. 5,162,602 and 5,498,544.

C. Genes for glyphosate resistance/tolerance. Gene of 5-enolpyruvyl-3-phoshoshikimate synthase (ES3P synthase) has been described in U.S. Pat. No. 4,769,601. Genes of 5-enolpyruvylshikimate-3-phosphate synthase (EPSPS) and mutants have been described in U.S. Pat. Nos. 4,940,835, 5,188,642, 5,310,667, 5,633,435, 5,633,448, and 6,566,587.

D. Genes for glufosinate (bialaphos, phosphinothricin (PPT)) resistance/tolerance. Gene for phosphinothricin acetyltransferase (Pat) has been described in U.S. Pat. Nos. 5,273,894, 5,276,268, and 5,550,318; and gene for bialaphos resistance gene (Bar) has been described in U.S. Pat. Nos. 5,561,236 and 5,646,024, 5,648,477, and 7,112,665. Gene for glutamine synthetase (GS) has been described in U.S. Pat. No. 4,975,372 and European patent application EP 0333033 A1.

E. Resistance/tolerance genes of hydroxy phenyl pyruvate dioxygenase (HPPD) against herbicides isoxazole, diketonitriles, and/or triketones including sulcotrione and mesotrione have been described in U.S. Pat. Nos. 6,268,549 and 6,069,115.

F. Genes for 2,4-D resistance/tolerance. Gene of 2,4-D-monooxygenase has been described in U.S. Pat. Nos. 6,100,446 and 6,153,401. Additional genes for 2,4-D resistance/tolerance are disclosed in US 2009/0093366 and WO 2007/053482.

G. Gene of imidazoleglycerol phosphate dehydratase (IGPD) against herbicides imidazole and/or triazole has been described in U.S. Pat. No. 5,541,310. Genes of Dicamba degrading enzymes (oxygenase, ferredoxin, and reductase) against herbicide Dicamba have been disclosed in U.S. Pat. Nos. 7,022,896 and 7,105,724.

H. Genes for herbicides that inhibit photosynthesis, including triazine (psbA and 1s+ genes) or a benzonitrile (nitrilase gene). See e.g., Przibila et al., Plant Cell 3:169 (1991) disclosing transformation of *Chlamydomonas* with plasmids encoding mutant psbA genes. Nucleotide sequences for nitrilase genes are disclosed in U.S. Pat. No. 4,810,648 and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

Unless otherwise specifically explained, all technical and scientific terms used herein have the same meaning as commonly understood by those of ordinary skill in the art to which this disclosure belongs. Definitions of common terms in molecular biology can be found in, for example: Lewin, Genes V, Oxford University Press, 1994 (ISBN 0-19-854287-9); Kendrew et al. (eds.), The Encyclopedia of Molecular Biology, Blackwell Science Ltd., 1994 (ISBN 0-632-02182-9); and Meyers (ed.), Molecular Biology and Biotechnology: A Comprehensive Desk Reference, VCH Publishers, Inc., 1995 (ISBN 1-56081-569-8).

Provided are constructs and methods relating to three EPSPS gene paralogs (A, B, and C) and their genetic components, such as 5' UTRs, promoters and transit peptides in *Brassica napus*. Also disclosed are transgenic and non-transgenic (in its native environment) uses of the genes and its genetic elements. In some embodiments, transgenic use of these genes or elements can confer traits of herbicide (for example, glyphosate or 2,4-D) tolerance in plant. Paralogs A and B share a high degree of homology or identity (~92%) and so do C and E (~95%). Paralog A is the highest expressing paralog in multiple tissue types and at different plant growth stages. The EPSPS paralog A gene is expressed constitutively in all tested plant tissues, for example leaves, roots, stems, apical meristem, flowers, flower buds etc, at 4-8 leaf stages. In addition, paralog A has a unique transit peptide sequence, compared to the other four paralogs. In some embodiments, the transit peptide of EPSPS paralog A is used to provide effective translocation of protein precursors from cytoplasm to plastids. Further, the transit peptide of EPSPS paralogs B, C and E can be useful to provide translocation of protein precursors from cytoplasm to plastids. The EPSPS enzymes represent the sixth key enzyme of the shikimate pathway for synthesis of aromatic amino acids and aromatic metabolite in plants, fungi and microorganisms. Hence the EPSPS genes can be up- or down-regulated in plants by any existing or future technologies which are applied to manipulate the amino acid content in plants. See, for example, WO 2009/042164, the content of which is incorporated by reference in its entirety. All of these features, either alone or in combination makes the EPSPS paralogs important for use in transgenic or non-transgenic (native gene environment) applications to confer traits such as herbicide tolerance and/or alterations in the amino acid, carbon and nitrogen contents as a result of the manipulation of the shikimate and associated pathways. Of special interest is transgenic canola according to the invention.

Provided is the promoter sequence of EPSPS paralog A from *B. napus* variety Nex710. This promoter of EPSPS paralog A is bidirectional based on results shown in transgenic *B. napus* callus tissue and plants, and is therefore designated as *Brassica* bidirectional constitutive promoter (BBCP). Use of BBCP in transgenic plants can provide at least one of the following advantages: (a) more genes can be stacked in one round of transformation into plant genome; (b) transgenes can be constitutively expressed in all plant tissues and parts; and (c) new genes can be further added or exchanged at the targeted locus with zinc finger-mediated precision gene stacking. For example, use of BBCP can enable expression of a selectable marker/herbicide resistance trait in one direction and a gene of interest (for example, trait of crop protection or yield enhancement) in another. Further provided is the unique transit peptide contained in the paralog A gene sequence to enable protein targeting to plastid for example chloroplast.

*B. napus* is an amphidiploid species resulting from the combination of two chromosome sets of *B. rapa* (2n=20, AA) and *B. oleracea* (2n=18, CC). Therefore, multiple EPSPS gene paralogs provided could either be homeologous or paralogous genes depending on their origin either from the A or C genomes (homeologous) or as a result of their duplication within a genome following speciation (paralogous).

Methods and constructs provided can be used to express any trait in canola or dicot/monocot plants, such as input traits (e.g., insect resistance and herbicide tolerance traits), agronomic traits (e.g., yield enhancement), output traits (e.g., healthy oil) etc. All methods pertaining to construction of specific vectors using BBCP and its transformation into canola or other plants are also provided.

Delivery and/or transformation: Suitable methods for transformation of plants include any method by which DNA can be introduced into a cell, for example and without limitation: electroporation (see, e.g., U.S. Pat. No. 5,384,253); microprojectile bombardment (see, e.g., U.S. Pat. Nos. 5,015,580, 5,550,318, 5,538,880, 6,160,208, 6,399,861, and 6,403,865); *Agrobacterium*-mediated transformation (see, e.g., U.S. Pat. Nos. 5,635,055, 5,824,877, 5,591,616; 5,981,840, and 6,384,301); and protoplast transformation (see, e.g., U.S.

Pat. No. 5,508,184). Through the application of techniques such as the foregoing, the cells of virtually any plant species may be stably transformed, and these cells may be developed into transgenic plants by techniques known to those of skill in the art. For example, techniques that may be particularly useful in the context of cotton transformation are described in U.S. Pat. Nos. 5,846,797, 5,159,135, 5,004,863, and 6,624,344; techniques for transforming Brassica plants in particular are described, for example, in U.S. Pat. No. 5,750,871; techniques for transforming soya are described, for example, in U.S. Pat. No. 6,384,301; and techniques for transforming maize are described, for example, in U.S. Pat. Nos. 7,060,876 and 5,591,616, and International PCT Publication WO 95/06722.

After effecting delivery of an exogenous nucleic acid to a recipient cell, the transformed cell is generally identified for further culturing and plant regeneration. In order to improve the ability to identify transformants, one may desire to employ a selectable or screenable marker gene with the transformation vector used to generate the transformant. In this case, the potentially transformed cell population can be assayed by exposing the cells to a selective agent or agents, or the cells can be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of the desired nucleic acid molecule comprising constructs provided in the regenerating plants, a variety of assays may be performed. Such assays may include: molecular biological assays, such as Southern and Northern blotting and PCR; biochemical assays, such as detecting the presence of a protein product, e.g., by immunological means (ELISA, Western blots, and/or LC-MS MS spectrophotometry) or by enzymatic function; plant part assays, such as leaf or root assays; and/or analysis of the phenotype of the whole regenerated plant.

Targeted integration events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (see, e.g., Rios et al. (2002) Plant J. 32:243-53), and may be applied to genomic DNA derived from any plant species or tissue type, including cell cultures. Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two may be produced. Thus, PCR genotyping strategies may include, for example and without limitation: amplification of specific sequences in the plant genome; amplification of multiple specific sequences in the plant genome; amplification of non-specific sequences in the plant genome; and combinations of any of the foregoing. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule, for example, at a sequence corresponding to a coding region within a nucleotide sequence of interest comprised therein, or other parts of the nucleic acid molecule. These primers may be used in conjunction with the primers described above. Oligonucleotide primers may be synthesized according to a desired sequence, and are commercially available (e.g., from Integrated DNA Technologies, Inc., Coralville, Iowa). Amplification may be followed by cloning and sequencing, or by direct sequence analysis of amplification products. One skilled in the art might envision alternative methods for analysis of amplification products generated during PCR genotyping. In one embodiment, oligonucleotide primers specific for the gene target are employed in PCR amplifications.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

EXAMPLES

Example 1

Identification of the EPSPS Paralog A Promoter (BBCP) Sequence

Five 5-enolpyruvyl shikimate-3-phosphate synthase (EPSPS) gene sequences (paralogs or homologues) in Brassica napus have been described in US 2009/0205083A1. Among these five genes, the promoter of the EPSPS paralog A drives strongest expression in various plant tissues. In order to expand the sequence of the 1571 nt EPSPS paralog A (SEQ ID NO: 7), additional sequences of the EPSPS paralog A gene are obtained via genome using a GenomeWalker™ universal kit (Clonetech Laboratories, Palo Alto, Calif.) to obtain the full sequence of the EPSPS paralog A (SEQ ID NO: 8) including its promoter region and the 3' untranslated region (for example SEQ ID NO: 26).

To identify promoter sequence of the EPSPS paralog A gene, the full sequence is searched using a Basic Local Alignment Search Tool (BLAST) against various plant and Brassica databases. Six cDNA and/or mRNA sequences of Brassica napus and Brassica rapa are identified that aligned in the direction of the EPSPS paralog A gene expression. The GenBank identification numbers (IDs) for these sequences are ES937178, ES904055, CD825798, CD835768, CD837464 and EV121915. These cDNA and/or mRNA sequences can be detected from leaf, root or embryo libraries of the target species but no specific role of these cDNA or mRNA has been annotated in GenBank. Interestingly, three cDNAs and/or mRNAs are identified matching the 5' sequence of EPSPS paralog A gene in the opposite direction to the expression of the EPSPS paralog A gene. The GenBank IDs of these sequences are: CD836095, EV100366 and EE568337. *Brassica napus* cDNA and/or mRNA sequences are the sources of these sequences, again with no specific function assigned to them in GenBank.

Sequence analysis of this example shows the promoter sequence of the EPSPS paralog A gene is a bidirectional promoter, which is designated as *Brassica* bidirectional constitutive promoter (BBCP).

Example 2

Design and Construction of BB CP Constructs

A single binary vector labeled as pDAB100333 is constructed using art recognized procedures. Binary pDAB100333 contains two sets of gene expression cassettes or Plant Transcription Units (PTUs). The first PTU set consists of the bi-directional *Brassica napus* Paralog A promoter (BBCP) which drives two reporter genes. One end of the BBCP is constructed to drive the expression of the β-glucuronidase reporter gene (GUS), and is terminated by the *Agrobacterium tumefaciens* open reading frame-24 3' untranslated region (AtuORF24 3'UTR). The opposite end of the BBCP is constructed to drive the green fluorescent protein reporter gene (GFP) and is terminated with the *Agrobacterium tumefaciens* nopaline synthase 3' untranslated region (Atu Nos 3'UTR).

The second PTU set of pDAB100333 includes a selectable marker cloned within the isopentenyltransferase coding sequence (ipt CDS; Genbank Acc No. X00639.1) thereby interrupting the jpt coding sequence, where the *Arabidopsis thaliana* Ubiquitin 10 promoter (AtUbi10 promoter) is used to drive the phosphinothricin acetyl transferase coding sequence (PAT), and the PTU is terminated by the *A. tumefaciens* open reading frame-1 3' untranslated region (AtuORF1 3'UTR). The resulting binary vector contains two visual reporter genes (GUS and GFP) driven by the bi-directional promoter and a selectable marker gene (PAT).

The binary vector, pDAB100333, is mobilized into *Agrobacterium tumefaciens* using electroporation. Individual colonies are identified on YEP media containing the antibiotic spectinomycin. Single colonies are isolated and the presence of the pDAB100333 binary vector can be confirmed via restriction enzyme digestion.

Another binary vector pDAB100331 is also constructed using art recognized procedures. Binary pDAB100331 is constructed to contain the BBCP in the reverse orientation as in pDAB100333 but with the same features as pDAB100333. Accordingly, binary vector pDAB100331 consists of two sets of gene expression cassettes or Plant Transcription Units (PTUs). The first PTU set consists of the bi-directional *Brassica napus* Paralog A promoter (BBCP in reverse orientation as compared to pDAB100333) which drives two reporter genes. One end of the BBCP is constructed to drive the green fluorescent protein reporter gene (GFP) and is terminated with the *Agrobacterium tumefaciens* nopaline synthase 3' untranslated region (Atu Nos 3'UTR). The opposite end of the BBCP is constructed to drive the expression of the β-glucuronidase reporter gene (GUS), and is terminated by the *Agrobacterium tumefaciens* open reading frame-24 3' untranslated region (AtuORF24 3'UTR).

The second PTU set of pDAB100331 also includes a selectable marker cloned within the isopentenyltransferase coding sequence (ipt CDS; Genbank Acc No. X00639.1) thereby interrupting the jpt coding sequence, where the *Arabidopsis thaliana* Ubiquitin 10 promoter (AtUbi10 promoter) is used to drive the phosphinothricin acetyl transferase coding sequence (PAT), and the PTU is terminated by the *A. tumefaciens* open reading frame-1 3' untranslated region (AtuORF1 3'UTR). The resulting binary vector contains two visual reporter genes (GUS and GFP) driven by the bi-directional promoter and a selectable marker gene (PAT).

Similarly, the binary vector, pDAB100331, is mobilized into *Agrobacterium tumefaciens* using electroporation. Individual colonies are identified on YEP media containing the antibiotic spectinomycin. Single colonies are isolated and the presence of the pDAB100331 binary vector can be confirmed via restriction enzyme digestion.

Direct DNA delivery vectors which are cloned into high copy number pUC based plasmids are constructed using only the first PTU containing the BBCP promoter which is described above. Plasmids pDAB108710 and pDAB108711 are constructed using art recognized procedures. The two vectors differ as they are constructed to contain the BBCP in the different orientation to drive the same features. The single PTU consists of the bi-directional *Brassica napus* paralog A promoter which drives two reporter genes. One end of the BBCP is constructed to drive the green fluorescent protein reporter gene (GFP) and is terminated with the *Agrobacterium tumefaciens* nopaline synthase 3' untranslated region (AtuNos 3'UTR). The opposite end of the BBCP is constructed to drive the expression of the β-glucuronidase reporter gene (GUS), and is terminated by the *Agrobacterium tumefaciens* open reading frame-24 3' untranslated region (AtuORF24 3'UTR). The direct DNA delivery vectors are used for particle bombardment of maize tissues.

Example 3

Expression of BBCP Construct in *Brassica napus*

Canola transformation—Preparation of hypocotyl segment and pre-treatment: Seeds of the elite canola genotype, Nex710, are surface-sterilized with 10% commercial bleach for 10 minutes and rinsed 3 times with sterile distilled water. The seeds are dried via a sterile paper towel then placed in a Phyta-tray containing "germination medium" consisting of one half concentration of MS basal medium [Phytotech Cat# M 519 (PhytoTechnology Laboratories, Shawnee Mission, Kans.)], 20 g/L sucrose, and 8 g/L TC Agar and maintained under growth regime set at 23° C. with a photoperiod of 16 hours light/8 hours dark.

On day five, seedlings are checked for sterility and the Phyta-tray is placed inside a laminar flow hood (The Baker Company EdgeGARD) to maintain sterility. Using sterile forceps and dissecting scissors, plants are removed from the Phyta-tray and the aerial (meristem and cotyledon) region and roots are detached and discarded. Hypocotyls are placed into a 100×25 mm petri dish containing sterile distilled water which is required to prevent drying. Hypocotyls are cut transversely into 2 mm segment, and lay horizontally on sterile filter paper over lay on "callus induction media MSK1D1" consisting of MS medium (Phytotech M519), 30 g/L sucrose, 1 mg/L kinetin, and 1 mg/L 2,4-D solidified with 7 g/L TC Agar. The plates are placed into a clear Sterilite® tub and maintained under the same growth regime for three days, as a pre-treatment.

Preparation of *Agrobacterium*: Four days before *Agrobacterium* infection, pDAB10333 and pDAB10331 in *Agrobacterium* strain DA2552 (see, for example, WO 2012/016222) are streaked out from a glycerol stock, on to YEP medium (10 g/L Peptone, 10 g/L Yeast Extract, 5 g/L NaCl, 10 g/L Sucrose plus 100 mg/L spectinomycin and 150 mg/L erythromycin and solidified with 15 g/L Bacto Agar) and grown for two days in an incubator (Fisher Scientific Isotemp Incubator) at 28° C. Two days after, a small loop of *Agrobacterium* is placed into a 500 mL sterile disposable baffled flask containing 150 mL "liquid bacterial growth medium" (same medium as above but minus solidifying agent). The culture is grown for sixteen hours at 28° C. in the dark on an enclosed shaker (New Brunswick Scientific Innova 4330 refrigerated incubator shaker) at 200 rpm. After sixteen hours the *Agrobacterium* culture is removed from the shaker and aliquoted into 50 mL centrifuge tubes. The centrifuge tubes are placed into a centrifuge (Beckman Model J2-21 centrifuge) and centrifuged at 6,000 rpm for 15 minutes and subsequently re-suspended in the "liquid culture medium M" consisting of LS salts (Phytotech L689), 3% glucose, modified Gamborg B5 vitamins (Phytotech G249), 215 mg/L Kinetin, and 221 mg/L 2,4-D at pH 5.

Infection and callus induction: On the day of infection, canola hypocotyl segments are transferred into a 100×25 sterile petri plate containing 20 mL of the "liquid culture medium" while waiting for *Agrobacterium* to be ready. The "liquid culture medium" is then removed from the hypocotyl segments and 40 mL of *Agrobacterium* suspension is vortexed briefly and poured into the 100×25 mm petri dish containing hypocotyl segments for a 30 minutes treatment. After the 30 minutes treatment, all of the *Agrobacterium* suspensions are removed using a double stacked pipette. The treated hypocotyls are placed back onto filter paper overlay on the "callus induction medium MSK1D1." The culture is returned to the Sterilite® tub, covered with a dark lid and returned to the culture room under the same growth regime as above, for a three days co-cultivation period. After the three days co-cultivation period, the hypocotyls are placed directly onto "selection 1 medium MSK1D1H1" (consisting of "callus induction medium" plus 1 mg/L Herbiace), placed back into the tub with a clear lid and returned to the culture room, maintaining the same growth regime as above. After one week, the hypocotyls are then transferred directly to "selection 2 medium MSK1D1H3" (consisting of "callus induction medium" plus 3 mg/L Herbiace). After two weeks, the hypocotyls are transferred to "selection 3 medium MSK1D1H5" (consisting of "callus induction media" plus 5 mg/l Herbiace). The hypocotyl segments are continued to be transferred every two weeks onto fresh selection 3 medium until enough callus are formed on the both ends of hypocotyls. The calluses are then assayed for GUS.

GUS stain of canola hypocotyl segments: The GUS stain procedure is known in the art with slight modification of GUS stain solution as follows: 0.1M $NaPO_4$ buffer at pH 8, 0.5 mM $K_3(Fe(CN)_6$, 10 mM $Na_2EDTA$, 1 mg/ml X-Gluc, and 0.06% Triton X-100. Chlorophyll from the stained tissue is removed by 70% ethanol. GUS assay is done in hypocotyl segments after being on selection 3 media for at least two weeks. The calli are immersed in GUS staining solution and incubated overnight in dark at 37° C. Uninfected tissue and GUS positive control are routinely included in the assay for negative and positive controls.

The results show significant GUS expression in transgenic callus samples obtained from both pDAB100331 and pDAB100333 transformation. No blue color is visible in non-transgenic control samples. Thus, the transgenic experimental results confirm that BBCP is a bidirectional promoter.

Example 4

Expression of BBCP Construct in Soybean

*Agrobacterium tumefaciens* strain EHA105 is electroporated with the binary vector pDAB9381 (a control binary vector which does not contain the BBCP bidirectional promoter), pDAB100331 and pDAB100333 separately. Isolated colonies are identified on YEP media containing the antibiotic spectinomycin. Single colonies are isolated and the presence of the pDAB9381, pDAB100331 and pDAB100333 binary vector can be confirmed via restriction enzyme digestion. *Agrobacterium*-mediated transformation of soybean (*Glycine max* c.v. Maverick) can be performed according to methods well known in the art.

After transformation, once roots are developed, the rooted plantlets are photographed for GFP expression with a 482 nm/502 nm GFP filter covering excitation/emission. Leaves are sampled from the plantlets for GUS staining according to the protocol adapted from Jefferson, R., (1987) "Histochemical localization of β-glucuronidase (GUS) reporter activity in plant tissues" Plant Mol. Biol. Reporter, 5: 387-405. Leaves are then immersed in staining solution comprised of: 2× Phosphate buffer pH7.0 (1× made of 0.1 M $NaH_2PO_4$ and 0.1 M $Na_2HPO_4$), 0.5 mM $K_3(Fe(CN)_6$, 10 mM $Na_2EDTA$, 1 mg/ml X-Gluc and 0.06% Triton X-100, and incubated overnight at 37° C. After incubation, staining solution is removed and tissue are washed with several changes of 70% ethanol and left overnight in ethanol before photographs are taken.

Results of four rounds of experiments are shown in Table 2 for explants and transgenic plantlets tested. Table 2 shows the number of transgenic shoots that are confirmed to contain expressed protein products of GFP and GUS reporter genes driven by BBCP. Soybean transgenic plants stably transformed with constructs pDAB100331 and pDAB100333 are regenerated with a frequency of 3-14%. Approximately 81-99% of the regenerated shoots (plantlets) express GFP while 41% of them express both GFP and GUS. In the plants regenerated with pDAB100333, GUS expression is more uniform throughout the leaf and not primarily expressed in the midrib tissue and veins. Comparatively in the plants regenerated from pDAB100331, GUS expression appears more localized in the midrib and veins of the leaves as observed in studies completed on multiple leaves. Transgenic plants transformed with a control construct, pDAB9381, do not show any GFP or GUS expression. The results confirm that the BBCP drives transgene expression in both directions at a reasonable level, although there might be some minor directional differences in the expression patterns within leaf tissue.

TABLE 2

GFP and GUS reporter genes expression by BBCP in explants and transgenic plantlets tested.

| Construct | No. of Explants infected | No. of shoots regenerated | No. of shoots showing GFP | No. of shoots showing GUS |
|---|---|---|---|---|
| pDAB9381 | 1096 | 246 (22.4%) | 236 (96%) | 0 |
| pDAB100331 | 1158 | 139 (12.0%) | 138 (99%) | 57 (41%) |
| pDAB100333 | 1153 | 160 (14.0%) | 154 (96%) | 63 (41%) |

Example 5

Transient Transformation of Maize Leaf Tissue

Tissue Preparation: Dark grown leaf tissue is harvested three to four hours prior to bombardment and placed on a bombardment preparation medium described in Table 3. Plates are wrapped and stored at 28° C. in dark until ready for bombardment.

Microparticles (gold) preparation: 30 mg gold (1 µm in size purchased from Bio-Rad, Hercules, Calif.) is washed in 500 µl cold ethanol, sonicated for fifteen seconds, and then vortexed for fifteen seconds. The particles are centrifuged for sixty seconds at 3000 rpm after settled for ten minutes. Supernatant is then discarded and pellet is washed with cold water (disrupt pellet with pipette tip and/or finger vortex) followed by centrifugation for sixty seconds at 3000 rpm. This wash and centrifugation step can be repeated two more times. After final rinse, 250 µl 50% glycerol (final concentration ~120 mg/ml) is added. The samples are sonicated for fifteen seconds, vortexed for fifteen seconds, and made aliquot into eppendorf tubes.

Preparing Microcarriers: For each plate of tissue to be bombarded, the gold/DNA reaction is prepared as follows: 5-15 µg DNA (plasmid pDAB108710, pDAB108711, or control plasmid DNA), 6 mg gold, final concentrations of 1 M $CaCl_2$ and 16 mM spermidine, in a total reaction volume of 125 µl. Immediately after sonicating and vortexing, 50 µl gold suspension aliquots are made into each reaction tube. The reaction tubes are vortexed before addition of 50 µl pre-chilled $CaCl_2$, and then vortexed again before addition of 20 µl 0.1 M Spermidine. The reaction tubes are then vortexed for up to ten minutes, and let sit for ten minutes on bench before centrifuge for fifteen seconds at 5000 rpm. Supernatant is discarded and pellets are resuspended in 150 µl 70% ethanol. Pellets are then disrupted with pipette and/or finger vortex before centrifuged for fifteen seconds at 5000 rpm. Supernatant is then discarded and pellets are resuspended in 150 µl ethanol. Pellets are then again disrupted with pipette and/or finger vortex before centrifuged for fifteen seconds at 5000 rpm. Finally, pellets are resuspended in 36 µl ethanol (36 µl per 6 mg gold) before bombardment experiment. Prior to aliquoting onto the microcarriers, pellets are sonicated for fifteen seconds and vortexed until the gold appears well suspended. Aliquot pellets onto the microcarriers for 10 µl each. Sonication and vortex between aliquots is recommended.

TABLE 3

Ingredients for bombardment preparation medium.

| Ingredient | Amount | Unit |
| --- | --- | --- |
| MS salts | 4.330 | g/L |
| 1,2,3,5/4,6-hexahydroxycyclohexane | 100.000 | mg/L |
| MES | 0.500 | g/L |
| EPS0000063-L-proline | 700.000 | mg/L |
| casein enzymatic hydrolysate | 100.000 | mg/L |
| sucrose | 30.000 | g/L |
| Gelzan (Gelrite) 714246 | 2.300 | g/L |
| EPS0000200-isu modified MS vitamin (1000×) | 1.000 | mL/L |
| EPS0000205-dicamba-KOH - 6.6 mg/ml | 3.300 | mg/L |
| EPS0000206-silver nitrate - 8.5 mg/ml | 15.000 | mg/L |
| Mannitol | 45.50 | g/L |

Bombardment Conditions: Helium-based microcarrier disks and a microcarrier holder are prepped and autoclaved prior to use. DNA-coated gold particles (10 µl well suspended) are placed on microcarriers for five minutes until dry. To assemble the microcarrier launch for shooting, the stop screen is first placed in the assembly unit. Then the microcarrier is placed upside-down on the assembly unit and then the assembly microcarrier lid is closed before a freshly and briefly rinsed (in 70% ethanol) 1350 psi rupture disk is placed in retaining cap and attached to the gas-acceleration tube. The microcarrier-assembly unit is then immediately placed at the top-level slot before chamber door is closed. Vacuum is activated in evacuation chamber before bombardment. Samples are bombarded by pressing and holding fire button until 1350 psi rupture disk bursts and helium pressure gauge drops to zero. Each plate can be bombarded up to three times with the same plasmid, where the plates can be turned so that the bombardment may take place at a different site/direction on the plate. After bombardment, plates are stored in the dark at 28° C. for at least twenty four hours before GFP observation and/or GUS staining using a Sigma-Aldrich staining kit.

Results: GUS expression is observed in leaf tissues bombarded with plasmids containing GUS gene driven by BBCP. Maize leaf tissues bombarded with a control plasmid do not show any GUS expression. GFP expression is observed in maize leaf samples transformed with plasmids having GFP gene driven by BBCP. Maize leaf tissues bombarded with a control construct do not show any GFP expression. The results confirm that BBCP is a bidirectional promoter driving expression of the reporter genes, GUS and GFP, in both directions. In conclusion, bidirectional expression from BBCP can be observed in both dicot (soybean and *B. napus*) and monocot (maize) plant tissues.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

We claim:

1. A nucleic acid construct for expressing multiple genes in plant cells and/or tissues, comprising,
    (a) a bi-directional promoter comprising a nucleotide sequence selected from SEQ ID NO: 2 or 3; and
    (b) two gene expression cassettes on opposite ends of the bi-directional promoter.

2. The nucleic acid construct of claim 1, wherein the bi-directional promoter comprises at least one enhancer.

3. The nucleic acid construct of claim 1, wherein the bi-directional promoter comprises at least one intron.

4. The nucleic acid construct of claim 1, wherein the bi-directional promoter comprises at least one 5' untranslated region.

5. The nucleic acid construct of claim 1, wherein at least one of the gene expression cassettes comprises two or more genes linked via a translation switch.

6. The nucleic acid construct of claim 1, wherein both the gene expression cassettes comprise two or more genes linked via a translation switch.

7. The nucleic acid construct of claim 5, wherein the translation switch is selected from the group consisting of an internal ribosome entry site (IRES), an alternative splicing site, a polynucleotide sequence coding a 2A peptide, a polynucleotide sequence coding a 2A-like peptide, a polynucleotide sequence coding an intein, a polynucleotide sequence coding a protease cleavage site, and combinations thereof.

8. The nucleic acid construct of claim 5, wherein a gene upstream of the translational switch does not comprise a translation stop codon.

9. The nucleic acid construct of claim 1, wherein the nucleic acid construct of comprises at least four transgenes.

10. The nucleic acid construct of claim 1, wherein the nucleic acid construct comprises between three and twenty transgenes.

11. The nucleic acid construct of claim 10, wherein the nucleic acid construct comprises between four and eight transgenes.

12. The nucleic acid construct of claim 1, wherein neither of the gene expression cassettes comprises an EPSPS coding sequence or paralog.

13. A method for generating a transgenic plant comprising transforming a plant cell with the nucleic acid construct of claim 1 and regenerating a transgenic plant comprising said construct from said plant cell.

14. A method for generating a transgenic plant cell, comprising transforming the cell with the nucleic acid construct of claim 1.

15. A plant cell comprising the nucleic acid construct of claim 1.

16. The plant cell of claim 15, wherein the nucleic acid construct is stably transformed into the plant cell.

17. A transgenic plant or seed comprising the nucleic acid construct of claim 1.

18. The transgenic plant or seed of claim 17, wherein the nucleic acid construct is stably transformed into cells of the transgenic plant or seed.

19. The transgenic plant of claim 17, wherein the transgenic plant is a dicotyledonous plant.

20. The transgenic plant of claim 17, wherein the transgenic plant is a monocotyledonous plant.

21. A method for expressing multiple genes in plant cells and/or tissues, comprising introducing into the plant cells and/or tissues the nucleic acid construct of claim 1.

22. The method of claim 21, wherein the plant cells and/or tissues are stably transformed with the nucleic acid construct of claim 1.

23. A binary vector for *Agrobacterium*-mediated transformation comprising the nucleic acid construct of claim 1.

24. A method for manufacturing transgenic seeds, comprising introducing the nucleic acid construct of claim 1 into a plant or plant cell, regenerating a transgenic plant from said cell, and collecting seeds from said plant, wherein said seeds comprise said nucleic acid construct.

25. The nucleic acid construct of claim 1, wherein the nucleotide sequence is SEQ ID NO: 2.

26. The nucleic acid construct of claim 1, wherein the nucleotide sequence is SEQ ID NO: 3.

* * * * *